United States Patent
Yeung et al.

(10) Patent No.: US 11,628,231 B2
(45) Date of Patent: Apr. 18, 2023

(54) STATIC AND MOBILE DISINFECTION USING HIGH INTENSITY NARROW WAVELENGTH ILLUMINATION

(71) Applicant: THE HONG KONG UNIVERSITY OF SCIENCE AND TECHNOLOGY, Hong Kong (CN)

(72) Inventors: King Lun Yeung, Hong Kong (CN); Qing Chang, Hong Kong (CN); Nga Ki Wong, Hong Kong (CN); Ning Zhan, Hong Kong (CN); Wei Han, Hong Kong (CN); Joseph Kai Cho Kwan, Hong Kong (CN); Javier Lopez Navas, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 200 days.

(21) Appl. No.: 16/843,279

(22) Filed: Apr. 8, 2020

(65) Prior Publication Data
US 2020/0230274 A1   Jul. 23, 2020

Related U.S. Application Data

(63) Continuation-in-part of application No. PCT/CN2018/109805, filed on Oct. 11, 2018.
(Continued)

(51) Int. Cl.
*A61L 2/10*   (2006.01)
*A61L 2/08*   (2006.01)
(Continued)

(52) U.S. Cl.
CPC ............... *A61L 2/10* (2013.01); *A61L 2/084* (2013.01); *A61L 2/085* (2013.01); *A61L 2/24* (2013.01);
(Continued)

(58) Field of Classification Search
CPC . A61L 2/10; A61L 2/085; A61L 2/084; A61L 2/24; A61L 2/26; A61L 2202/11; A61L 2202/14; A61L 2202/16
See application file for complete search history.

(56) References Cited

U.S. PATENT DOCUMENTS

| 8,088,289 B2 | 1/2012 | Tribelsky |
| 8,105,532 B2 | 1/2012 | Harmon et al. |

(Continued)

FOREIGN PATENT DOCUMENTS

| CN | 102563384 A | 7/2012 |
| CN | 103212161 A | 7/2013 |

(Continued)

OTHER PUBLICATIONS

Gillespie, et al., "Efficacy of Pulsed 405-nm Light-Emitting Diodes for Antimicrobial Photodynamic Inactivation: Effects of Intensity, Frequency, and Duty Cycle", Photomedicine and Laser Surgery, vol. 35, No. 3, pp. 150-156, 2017.
(Continued)

*Primary Examiner* — Sean E Conley
(74) *Attorney, Agent, or Firm* — Nath, Goldberg & Meyer; Joshua B. Goldberg

(57) ABSTRACT

Microbial disinfection is performed using continuous or intermittent lighting using one or more narrow wavelength light sources. The light sources illuminate with narrow wavelength characteristics. The lighting provides a sufficiently high intensity for rapid microbial disinfection process, while reducing the average energy consumption for microbial disinfection during the microbial disinfection process by targeting multiple cellular sites along different inactivation pathways.

20 Claims, 23 Drawing Sheets

Related U.S. Application Data

(60) Provisional application No. 62/920,135, filed on Apr. 15, 2019, provisional application No. 62/606,850, filed on Oct. 11, 2017.

(51) Int. Cl.
  *A61L 2/24* (2006.01)
  *A61L 2/26* (2006.01)

(52) U.S. Cl.
  CPC .............. *A61L 2/26* (2013.01); *A61L 2202/11* (2013.01); *A61L 2202/14* (2013.01); *A61L 2202/16* (2013.01)

(56) References Cited

U.S. PATENT DOCUMENTS

| | | | |
|---|---|---|---|
| 8,481,985 | B2 | 7/2013 | Neister |
| 9,144,617 | B2 | 9/2015 | Deng |
| 9,247,882 | B2 | 2/2016 | Hakomori et al. |
| 9,333,274 | B2 | 5/2016 | Peterson et al. |
| 9,439,989 | B2 | 9/2016 | Lalicki et al. |
| 9,550,005 | B2 | 1/2017 | Lin et al. |
| 9,707,307 | B2 * | 7/2017 | Shur ................. A23L 3/003 |
| 2004/0256581 | A1 | 12/2004 | Au et al. |
| 2017/0080117 | A1 * | 3/2017 | Gordon ............. A61L 2/10 |
| 2018/0093107 | A1 * | 4/2018 | Ball ................. A61N 5/0616 |

FOREIGN PATENT DOCUMENTS

| | | |
|---|---|---|
| CN | 105214113 A | 1/2016 |
| WO | 2005/077121 A2 | 8/2005 |
| WO | 2015/066238 A3 | 5/2015 |
| WO | 2015/116876 A1 | 8/2015 |
| WO | 2016/168139 A1 | 10/2016 |

OTHER PUBLICATIONS

Barenfaller, et al., "Effect of photoactivated disinfection using light in the blue spectrum", Journal of Photochemistry & Photobiology, B: Biology, vol. 158, pp. 252-257, 2016.

Leite, et al., "Effects of Photodynamic Therpay with Blue Light and Curcumin as Mouth Rinse for Oral Disinfection: A Randomized Controlled Trial", Photomedicine and Laser Surgery, vol. 32, No. 11, 2014.

Goodman, et al., "Impact of an Environmental Cleaning Intervention on the Presence of Methicillin-Resistant *Staphylococcus aureus* and Vancomycin-Resistant Enterococci on Surfaces in Intensive Care Unit Rooms", Infection Control and Hospital Epidemiology, vol. 29, No. 7, 2008.

Boyce, et al., "Environmental Contamination Due to Methicillin-Resistant *Staphylococcus aureus*: Possible Infection Control Implications", Infection Control and Hospital Epidemiology, 1997.

Dancer, "Hospital Cleaning in the 21st century", Eur J Clin Microbiol Infect Dis, vol. 30, pp. 1473-1481, 2011.

Hota, "Contamination, Disinfection, and Cross-Colonization: Are Hospital Surfaces Reservoirs for Nosocomial Infection?", Healthcare Epidemiology, CID 2004:39, 2004.

Siegel, et al., "2007 Guideline for Isolation Precautions: Preventing Transmission of Infectious Agents in Healthcare Settings", http://www.cdc.gov/ncidod/dhqp/pdf/isolation2007.pdf.

Miyachi, et al., "Controlling methicillin-resistant *Staphylococcus aureus* by stepwise implementation of preventive strategies in a university hospital: impact of a link-nurse system on the basis of multidisciplinary approaches", 2007.

Asai, et al., "Differential Coexpression of Mex Efflux Pumps in a Clinical Strain of Metallo-B-lactamase-Producing Pseudomonas aeruginosa During the Stepwise Evolution of Resistance to Aminoglycosides", Infectious Diseases in Clinical Practice, vol. 19, No. 1, 2011.

Eckstein, et al., "Reduction of Clostridium Difficile and vancomycin-resistant Enterococcus contamination of environmental surfaces after an intervention to improve cleaning methods", BMC Infectious Disease, No. 7, No. 61, 2007.

Hayden, et al., "Reduction in Acquisition of Vancomycin-Resistant Enterococcus after Enforcement of Routine Environmental Cleaning Measures", Clinical Infectious Diseases vol. 42, pp. 1552-1560, 2006.

Lessa, et al., "Health Care Transmission of a Newly Emergent Adenovirus Serotype in Health Care Personnel at a Military Hospital in Texas, 2007", The Journal of Infectious Diseases, vol. 200, pp. 1759-1765, 2009.

McArdle, et al., "How much time is needed for hand hygiene in intensive care? A prospective trained observer study af rates of contact between healthcare workers and intensive care patients", Journal of Hospital Infection, vol. 62, pp. 304-310, 2006.

Pittet, et al., "Bacterial Contamination of the Hands of Hospital Staff During Routine Patient Care", Arch Intern Med, vol. 159, pp. 821-826, 1999.

Pittet, et al., "Evidence-based model for hand transmission during patient care and the role of improved practices", Lancet Infect Dis, vol. 6, pp. 641-652, 2006.

Fraise, et al., "Choosing disinfectants", Journal of Hospital Infections, vol. 43, pp. 255-264, 1999.

Hardy, et al., "Rapid recontamination with MRSA of the environment of an intensive care unit after decontamination with hydrogen peroxide vapour", Journal of Hospital Infection, No. 66, pp. 360-368, 2007.

Grass, et al., "Metallic Copper as an Antimicrobial Suface", Applied and Environmental Microbiology, vol. 77, No. 5, pp. 1541-1547, 2011.

Dai, et al., Ultraviolet C irradiation: an alternative antimicrobial approach to localized infections?, Expert Rev Anti Infect Ther., vol. 10, No. 2, pp. 185-195, 2012.

Gurzadyan, et al., "Ultraviolet (193, 216 and 254 nm) Photoinactivation of *Escherichia coli* Strains with Different Repair Deficiencies", Radiation Research, vol. 141, pp. 244-251, 1995.

Caminiti, et al., "The Effect of Ultraviolet Light on Microbial Inactivation and Quality Attributes of Apple Juice", Food Bioprocess Technol, vol. 5, pp. 680-686, 2012.

Char, et al., "Use of High-Intensity Ultrasound and UV-C Light to Inactivate Some Microorganisms in Fruit Juices", Food Bioprocess Technol, vol. 3, pp. 797-803, 2010.

Donahue, et al., "UV Inactivation of *E. coli* O157:H7 in Apple Cider: Quality, Sensory and Shelf-Life Analysis", Journal of Food Processing and Preservation, vol. 28, pp. 368-387, 2004.

Gabriel, et al., "Inactivation of *Salmonella, E. coli* and *Listeria monocytogenes* in phosphate-buffered saline and apple juice by ultraviolet and heat treatments", Food Control, vol. 20, pp. 443-446, 2009.

Oteiza, et al., "Ultraviolet Treatment of Orange Juice to Inactivate *E. coli* O157:H7 as Affected by Native Microflora", Food Bioprocess Technol, vol. 3, pp. 603-614, 2010.

Keyser, et al., "Ultraviolet radiation as a non-thermal treatment for the inactivation of microorganisms in fruit juice", Innovative Food Science and Emerging Technologies, vol. 9, pp. 348, 354, 2008.

Fredericks, et al., "Efficacy of ultraviolet radiation as an alternative technology to inactivate microorganisms in grape juices and wines", Food Microbiology, vol. 28, pp. 510-517, 2011.

Bandla, et al., "UV-C treatment of soymilk in coiled tube UV reactors for inactivation of *Escherichia coli* W1485 and Bacillus cereus endospores", LWT—Food Science and Technology, vol. 46, pp. 71-76, 2012.

Nardell, et al., "Safety of Upper-Room Ultraviolet Germicidal Air Disinfection for Room Occupants: Results from the Tuberculosis Ultraviolet Shelter Study", Public Health Reports, vol. 123, 2008.

Ko, et al., "Influence of relative humidity on particle size and UV sensitivity of Serratia marcescens and Mycobacteriumm bovis BCG aerosols", Tubercle and Lung Disease, vol. 80, No. 4/5, pp. 217-228, 2000.

Peccia, et al., "Effects of Relative Humidity on the UV-Induced Inactivation of Bacterial Bioaerosols" J Aerosol Sci, vol. 31, Suppl. 1, pp. S959-S960, 2000.

(56) References Cited

OTHER PUBLICATIONS

Peccia, et al., "Effects of Relative Humidity on the Ultraviolet Induced Inactivation of Airborne Bacteria", Aerosol Science and Technology, vol. 35, pp. 728,740, 2001.
Maclean, et al., "Environmental decontamination of a hospital isolation room using high-intensity narrow-spectrum light", Journal of Hospital Infection, No. 76, pp. 247-251, 2010.
Ashkenai, et al., "Eradication of Propionibacterium acnes by its endogenic porphyrins after illumination with high intensity blue light", FEMS Immunology and Medical Microbiology, vol. 35, pp. 17-24, 2003.
Hamblin, et al., "Helicobacter pylori Accumulates Photoactive Porphyrins and Is Killed by Visible Light", Antimicrobial Agents and Chemotherapy, pp. 2822-2827, 2005.
Maclean, et al., "The role of oxygen in the visible-light inactivation of *Staphylococcus aureus*", Journal of Photochemistry and Photobiology, vol. 92, pp. 180-184, 2008.
Tisch, et al., "Light regulation of metabolic pathways in fungi", Appl Microbiol Biotechnol, vol. 85, pp. 1259-1277, 2010.
Feuerstein, et al., "Mechanism of Visible Light Phototoxicity on Porphyromonas gingivalis and Fusobacterium nucleatum", Photochemisty and Photobiology, vol. 81, pp. 1186-1189, 2005.
Kim, et al., "In Vitro Bactericidal Effects of 625, 525, and 425 nm Wavelength (Red, Green, and Blue) Light-Emitting Diode Irradiation", Photomedicine and Laser Surgery, vol. 31, No. 11, pp. 554-562, 2013.
Lipovsky, et al., "Visible Light-Induced Killing of Bacteria as a Function of Wavelength: Implication for Wound Healing", Lasers in Surgery and Medicine, vol. 42, pp. 467-472, 2010.
Enwemeka, et al., "Visible 405 nm SLD Light Photo-Destroys Methicillin-Resistant *Staphylococcus aureus* (MRSA) In Vitro", Lasers in Surgery and Medicine, vol. 40, pp. 734-737, 2008.
Kawada, et al., "Acne phototherapy with a high-intensity, enhanced, narrow-band, blue light source: an open study and in vitro investigation", Journal of Dermatologist Science, vol. 30, pp. 129-135, 2002.
Maclean, et al., "High-intensity narrow-spectrum light inactivation and wavelength sensitivity of *Staphylococcus aureus*", FEMS Microbial Letter, vol. 285, pp. 227-232, 2008.
Maclean, et al., "Inactivation of Bacterial Pathogens following Exposure to Light from a 405-Nonometer Light-Emitting Diode Array", Applied and Environmental Microbiology, vol. 75, No. 7, pp. 1932-1937, 2009.
Soukos, et al., "Phototargeting Oral Black-Pigmented Bacteria", Antimicrobial Agents and Chemotherapy, vol. 49, No. 4, pp. 1391-1396, 2005.
Yoshioka, et al., "Specific-wavelength visible light irradiation inhibits bacterial growth of Porphyromonas gingivalis", Journal of Periodontal Research, vol. 43, pp. 174-178, 2008.
Gold, et al., "Clinical Efficacy of Self-applied Blue Light Therapy for Mild-to-Moderate Facial Acne", J Clin Aesthetic Dermatol., vol. 2, No. 3, pp. 44-50, 2009.
Kleinpenning, et al., "Clinical and histological effects of blue light on normal skin", Photodermatology, Photoimmunology & Photomedicine, vol. 26, pp. 16-21, 2010.
Dai, et al., "Blue light for infectious diseases: Propionibacterium acnes, Helicobacter pylori, and beyond?", Drug Resist Updat. vol. 15, No. 4, pp. 223-236, 2012.
United Nations Environmental Programme (UNEP), Environmental effects of ozone depletion: 1998 Assessment, 1998.
Tsen, et al., "Inactivation of viruses by coherent excitations with a low power visible femtosecond laser", Virology Journal, vol. 4, No. 50, 2007.
Tsen, et al., "Inactivation of viruses by laser-driven coherent excitations via impulsive stimulated Raman scattering process", Journal of Biomedical Optics, vol. 12, No. 6, 2007.
Tsen, et al., "Photonic approach to the selective inactivation of viruses with a near infrared subpicosecond fiber laser", Journal of Biomedical Optics, vol. 14, No. 6, 2009.
Tsen, et al., "Inactivism of viruses with a very low power visible femtosecond laser", Journal of Physics Condensed Matter, vol. 19, 2007.
Tsen, et al., "Selective inactivation of micro-organisms with near-infared femtosecond laser pulses", Joural of Physics: Condenced Matter, vol. 19, 2007.
Tsen, et al., Studies of inactivation of encephalomyocarditis virus, M13 bacteriophage, and *Salmonella typhimurium* by using a visible femtosecond laser: insight into the possible inactivation mechanisms, Journal of Biomedical Optics, vol. 16, No. 7, 2011.
Bornstein, et al., "Near-infrared Photoinactivation of Bacteria and Fungi at Physiologic Temperatures", Photochemistry and Photobiology, vol. 85, pp. 1364-1374, 2009.
Krespi, et al., "Laser-assisted nasal decolonization of *Staphylococcus aureus*, including methicillin-resistant *Staphylococcus aureus*", American Journal of Otolaryngology: Head and Neck Medicine and Surgery, vol. 33, pp. 572-575, 2012.
Umezawa, et al., "A Comparative Study of the Bactericidal Activity and Daily Disinfection Housekeeping Surfaces by a New Portable Pulsed UV Radiation Device", Curr Microbiol, vol. 64, pp. 581-587, 2012.
Leibert, "Effects of photodynamic therapy with blue light and curcumin as mouth rinse for oral disinfection: a randomized controlled trial", Photomedicine and Laser Surgery, vol. 32, No. 11, pp. 627-632, 2014.
Carling, et al., "Improved Cleaning of Patient Rooms Using a New Targeting Method", Clinical Infectious Diseases, vol. 42, pp. 385-388, 2006.
Qureshi, et al., "Role of Ultraviolet (UV) Disinfection in Infection Control and Environmental Cleaning", Infectious Disorders—Drug Targets, vol. 13, pp. 191-195, 2013.
Knudson, et al., "Pulsed UV light disinfection system shows promise for OR decontamination", AORN Connections, vol. 98, No. 5, 2013.

\* cited by examiner

| Treatment group | Waveform |
|---|---|
| Scheme 1: UV only |  |
| Scheme 2: Pre-exposure to 405nm (405nm then UV illumination) |  |
| Scheme 3: Post-exposure to 405nm (UV illumination then 405nm) |  |
| Scheme 4: Pre-exposure to 470nm (470nm then UV illumination) |  |
| Scheme 5: Post-exposure to 470nm (UV illumination then 470nm) |  |
| Scheme 6: Alternative exposure to 405nm |  |
| Scheme 7: Alternative exposure to 470nm |  |

STATIC AND MOBILE DISINFECTION USING HIGH INTENSITY NARROW WAVELENGTH ILLUMINATION

RELATED APPLICATIONS

The present Patent Application claims priority to PCT Application No. PCT/CN2018/109805, filed Oct. 11, 2018, published as WO/2019/072205. PCT/CN2018/109805 claims priority to Provisional Patent Application No. 62/606,850 filed Oct. 11, 2017. The present Patent Application also claims priority to Provisional Patent Application No. 62/920,135, filed Apr. 15, 2019. The above patent applications are assigned to the assignee hereof, and are incorporated by reference herein.

BACKGROUND

Technical Field

This disclosure relates to light disinfection technology used for inactivating microorganisms. More particularly, the disclosure is directed to static and mobile disinfection devices combining different light sources to rapidly disinfect antibiotic-resistant bacteria on soft and rigid surfaces and in the liquid phase as well as viruses and spores.

Background

Contact with contaminated surfaces is the most common transmission route of infectious diseases. Environmental surfaces play an important role in transmission of hospital-acquired infections (HAI), which are infections that are acquired in healthcare settings. Surfaces in the patient-care areas with microbiological contamination can serve as reservoirs for potential pathogens responsible for HAI. Such microorganisms include Methicillin-resistant *Staphylococcus aureus* (MRSA), multi-drug-resistant *Pseudomonas aeruginosa* (MRPA), vancomycin-resistant *Enterococci* (VRE) and others. There are several published guidelines for preventing infectious transmission between patients. The U.S. Centers for Disease Control and Prevention recommends routine environmental decontamination of surfaces in the patient area by cleaning and disinfection as a part of the standard precaution for preventing transmission of infectious agents in healthcare settings.

Hospital-acquired infection (HAI) is becoming an important cause of mortality and morbidity in hospitals. As an indication of the significance of the mortality, in the United States alone, HAI accounts for close to $10 billion in additional annual health care costs. Reports show that depending on the surgical procedure between 0.5 to 10 percent of all clean surgeries in the United States or close to about 275,000 patients each year result in surgical site infections (SSI). The annual number of deaths attributed to SSI in the US has been estimated at 8,200 with an annual patient hospital cost of between $3 and $10 billion. The preponderance of the HAI and SSI cases are caused by multi-drug-resistant microbes making it a global concern of escalating importance in term of cost and patient safety. Hospitals are becoming an important source of acquisition and spread of pathogens among hospitalized patients. The situation is aggravated by the fact that many multi-drug-resistant microorganisms (MDRO) including methicillin-resistant *Staphylococcus aureus* (MRSA), multi-drug-resistant *Pseudomonas aeruginosa* (MRPA), imipenem-resistant *Acinetobacter*, vancomycin-resistant *Enterococci* (VRE), *Clostridium difficile* and fungi are known to persist in hospital environment for days and weeks.

Decontaminating high-touch surfaces is seen as a way of reducing HAI. Manual cleaning with approved disinfectants is the current standard of disinfection in most countries; however, this requires supervision with constant reinforcement and education of environmental management service staff to maintain effectiveness. Studies have identified substantial opportunities in hospitals to improve the cleaning of frequently touched surfaces in the patient's immediate environment. The use of chemical disinfectants such as sodium hypochlorite, ozone, hydrogen peroxide and antimicrobial metals also brings the issues of material compatibility (i.e., surface damage and corrosion), emergence of microbial tolerance and resistance, and persistence of potential harmful residues. There is therefore an urgent need to develop alternate surface disinfection technologies that are not only safe and effective against a wide spectrum of microorganisms including the drug-resistant infectious microbes, but also prevent the emergence of tolerance or resistance in the microorganism.

Poor hand hygiene compliance is also a significant source of surface contamination and is an important risk factor for outbreaks. In the hospital environment, surfaces with which hands come in contact are often contaminated with nosocomial pathogens and may serve as vectors for cross-transmission. A single incidence of hand contact with a contaminated surface results in a variable degree of pathogen transfer. Studies showed that transmission to hands was most successful with *E. coli* and *S. aureus*. Contaminated hands can transfer viruses to five more surfaces or 14 other subjects and can also be the source of recontamination of the surface too. Furthermore, surface cleaning is often suboptimal, performed by manually applying a liquid disinfectant (e.g., ethanol or hypochlorite) on the surface with a cloth. More stringent approaches using bactericidal metals and $H_2O_2$ vapor are shown to be effective, but are harsh on the surface and leave behind harmful residues.

Manual cleaning with approved disinfectants is the current disinfection standard in most countries, and this requires supervision with constant reinforcement and education of environmental management service staff to maintain effectiveness. The development of more effective surface decontamination methods has attracted much attention. Hydrogen peroxide vapor decontamination, ozone disinfection, steam cleaning and the use of microfiber clothes and antimicrobial metals such as copper have been explored as alternative disinfection methods. These techniques also bring some concerns such as material compatibility (i.e., surface damage and corrosion), emergence of microbial tolerance and resistance, and persistence of potential harmful residues. There is therefore an urgent need to develop alternate surface disinfection technologies that are not only safe and effective against a wide spectrum of microorganisms including the drug-resistant infectious microbes, but which also avoids promoting the development of resistance in the target microorganisms.

Previous light disinfection techniques used a single light source (UV, blue light or germicidal light) or used several light sources to output white light. Light-based disinfection technology using ultraviolet (UV, 100-400 nm) irradiation has been widely investigated. Among the four spectral regions of UV light that include vacuum UV (100-200 nm), UVC (200-280 nm), UVB (280-315 nm) and UVA (315-400 nm), UVC is the most effective for inactivation of microorganisms. The UVC wavelengths of 250-270 nm are strongly absorbed by the nucleic acids of the microbial cells causing damages to the RNA and DNA molecules. This involves the dimerization of the pyrimidine residues in the nucleic acid strands producing cyclobutane pyrimidine dimes (CPDs) that deforms the RNA and DNA molecules causing defects in cell replication that eventually leads to cell death. UVC disinfection is popular in food industries and is shown to be effective against food-borne pathogens. The effect of this on a variety of food products including fruit juices, fruit nectars, wine and soymilk have been studied. UVC is employed in the current World Health Organization (WHO) tuberculosis (TB) infection control plan in the form of upper-room ultraviolet germicidal irradiation (UVGI). UVGI can rapidly treat a large volume of room air at a relatively low cost, but its deployment can be difficult due to the current fixture designs. Low-pressure mercury vapor discharge lamps emitting 253.7 nm UV light (germicidal lamps) are mounted on an upper wall or suspended from the ceiling of the room. In order to minimize UV radiation exposure that can potentially cause eye or skin irritations to the room occupants, closely spaced, deep louvers are used to collimate or deflect the UV beam so it is nearly parallel to the ceiling. Humidity has been shown to be detrimental to the effectiveness of UVGI and may require the use of higher lamp intensities in humid places.

More recent studies showed that blue light (400-500 nm) has intrinsic antimicrobial activities against many of the drug-resistant bacteria. The antimicrobial mechanism of blue light remains poorly understood, but it is commonly accepted that blue light excites endogenous intracellular porphyrins in many bacteria and the flavoproteins and flavins found in fungal cells. The resulting photon absorption results in a cascade of energy transfer that ultimately leads to the production of highly cytotoxic reactive oxygen species (ROS)—most notably singlet oxygen ($^1O_2$). Blue light is active against a wide variety of gram-positive and gram-negative bacteria. Studies showed that blue light with the wavelengths of 402-420 nm, 455 or 470 nm has the highest bactericidal activity. Blue light has been shown to be safe in a clinical study with volunteers exposed to high doses of it. Laboratory studies on mammalian cells gave similar conclusion. Exposure to blue light did not appear to cause damage to materials (i.e., plastic) that is often associated to UV light exposure.

A series of studies have shown that a femtosecond pulsed light source with a wavelength between 600 to 900 nm is effective against viruses such as M13 bacteriophage, tobacco mosaic virus, HPV, and human immunodeficiency virus (HIV). The technique delivers an intense packet of photon energy (10 mW) for a very short time (100 fs) to generate 100 GW pulsed energy that is sufficient to produce efficient two-photon absorption. The technique is non-invasive, safe and highly selective for disinfection of pathogens. Exposure to dual-wavelength light source at near infrared can inactivate many bacteria and fungi including S. aureus, E. coli, C. albicans and T. rubrum. A study also showed that it could also re-sensitize drug-resistant microorganism to common antibiotic and the process is believed to be caused by light-mediated changes in the microbial respiratory processes in the cellular membrane that also interferes with the bacterial resistance mechanism. These studies show beyond doubt that many microorganisms are photosensitive and can interact and respond to light in different manners. Although the exact mechanisms are not well understood, it is clear that there are ample opportunities for using light to mitigate microbial contamination in health-care settings.

SUMMARY

Microbial disinfection is performed by providing continuous lighting, asynchronous intermittent lighting or synchronous intermittent lighting using one or more narrow wavelength light sources. At least one of the light sources has a narrow wavelength characteristic consistent with the spectral widths of single color LEDs. The lighting provides a sufficiently high intensity for rapid microbial disinfection process, while reducing the average energy consumption for microbial disinfection during the microbial disinfection process by targeting multiple cellular sites along different inactivation pathways.

BRIEF DESCRIPTION OF THE DRAWINGS

FIG. 2A samples P. aeruginosa. FIG. 2B samples E. coli. FIG. 2C samples S. aureus. FIG. 2D samples E. faecalis.

FIG. 3A shows efficacy of UV (280 nm) LED illumination. FIG. 3B shows efficacy of UVC fluorescent light illumination.

FIG. 6A shows efficacy against P. aeruginosa. FIG. 6B shows efficacy against E. coli. FIG. 6C shows efficacy against S. aureus. FIG. 6D shows efficacy against E. faecalis. FIG. 6E shows the applied continuous (100%) and pulsed (50%) waveforms.

FIG. 8A shows cytotoxicity at different dosages for UV (280 nm) light. FIG. 8B shows cytotoxicity for 405 nm and 470 nm blue lights.

FIG. 10A shows the illumination frequencies. FIG. 10B samples P. aeruginosa. FIG. 10C samples E. coli. FIG. 10D samples S. aureus. FIG. 10E samples E. faecalis.

FIG. 11A shows the duty cycles of the applied waveforms. FIG. 11B samples P. aeruginosa. FIG. 11C samples E. coli. FIG. 11D samples S. aureus. FIG. 11E samples E. faecalis.

FIG. 15A samples *S. aureus*. FIG. 15*b* samples *P. aeruginosa*.

FIG. 16A samples *P. aeruginosa*. FIG. 16B samples *S. aureus*.

FIG. 18A shows the waveforms applied against *E. coli* bacteriophage T3. FIG. 18B shows the virucidal activities against *E. coli* bacteriophage T3. FIG. 18C shows the sporicidal activities against *Aspergillus niger*.

DETAILED DESCRIPTION

Overview

Figure 1A:
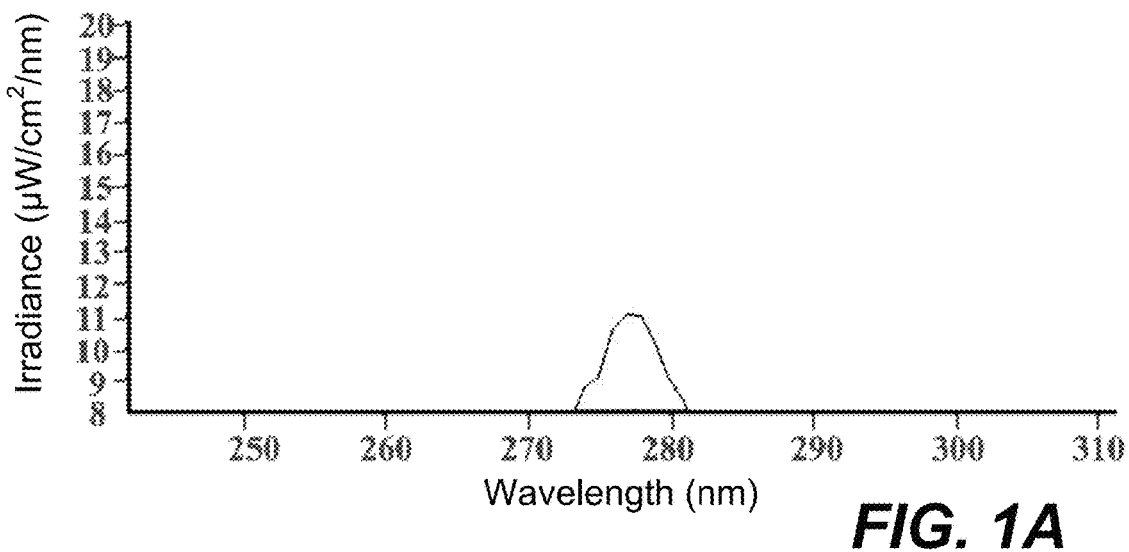
FIGS. 1A-1D are graphic diagrams showing emission spectra of UV (280 nm) LED (FIG. 1A) and UVC fluorescent light (FIGS. 1B-1D).

The disclosed technology describes a new light disinfection technology based on asynchronous, intermittent lighting using high intensity, narrow wavelength light sources for rapid microbial disinfection at low energy consumption and improved safety. The disclosed technology teaches the use of optimum combination of lighting and a light exposure program to rapidly inactivate microorganisms by targeting multiple cellular sites along different inactivation pathways. A hand-held and autonomous robot-type configurations of light-based disinfection devices can be used for disinfection by using static, rotatory, movable rail-type and automatic switching light sources for the applications in small spaces (such as container, drawer and biosafety cabinet), indoor, corridor or the sites frequently contaminated by microorganisms.

For the purposes of the disclosed technology, "narrow wavelength light" means light having a light frequency range that is useful for targeted germicidal purposes, consistent with the light output of a single-color LED light. More broadly, "narrow wavelength light" can refer to light having a spectral width of <100 nm. A non-limiting example of narrow wavelength light is a 253.7 nm low pressure mercury vapor gas-discharge germicidal lamp; however, the spectrum of a single color LED light is also sufficiently narrow for the purposes described here. The emission pattern of single color LED lights is a non-limiting example of a narrow wavelength. By way of non-limiting example, LEDs are typically available with −3 dB spectral widths in the range of 24 to 27 nm, with a wider spectral width −3 dB being 50 to 180 nm or 40 to 190 nm. These spectral widths are narrow, but not as narrow as that of a 253.7 nm germicidal lamp. In a non-limiting example, the spectral width is narrower than 100 nm.

In one non-limiting example, narrow spectral width light may be light having a spectral width of <100 nm, an illumination rate of 0.1 Hz to 1000 Hz, and a duty cycle of 1% to 99%. More broadly, the light may have narrower ranges of operation, for example an illumination rate of 0.1 Hz to 100 Hz, and/or a duty cycle of 10% to 99%. In one non-limiting example, the lighting may be used comprising of UV at approximately 280 nm and light at approximately 405 nm and approximately 470 nm, produced by LED bulbs having a spectral width of <100 nm, an illumination rate of 0.1 Hz to 100 Hz, and a duty cycle of 10% to 99%.

The disclosed technology combines multiple light sources with different wavelengths, and adjusts exposure time, frequency, duty cycle and lighting pattern of different light sources to achieve rapid surface disinfection. The present disclosure relates to light disinfection technology based on asynchronous, intermittent lighting using high intensity, narrow wavelength light sources for rapid microbial disinfection at low energy consumption and improved safety. In an embodiment, a lighting system comprising a 405 nm LED, a 470 nm LED and four UV LEDs is used to generate synchronous and asynchronous light patterns. The highly bactericidal efficacy system is powered by three 4 V rechargeable batteries and controlled by a circuit with a programmed microcontroller (Arduino) and a monitor to adjust exposure time, frequency, duty cycle and lighting pattern.

LED lights have particular advantages in that they quickly respond to power application, allowing more easily controlled duty cycles than other forms of lighting. LEDs provide high lighting efficiencies, typically 15%-50%, with a theoretical range of 38.1-43.9% with phosphorescence, and higher without phosphorescence color mixing. In contrast, metal halide and high and low pressure sodium gas-discharge lamps and mercury vapor gas-discharge lamps have efficiencies ranging from 9.5-29%. LEDs are more easily controlled and have shorter duty cycles than other some other forms of lighting. As applied to the disclosed technology, the LEDs can be either direct emitting or use phosphorescence to achieve the desired wavelength emissions.

In a further embodiment, the disclosed technology is directed to the use of an optimum combination of light source and a light exposure program to rapidly inactivate microorganisms by targeting multiple cellular sites along different inactivation pathways.

It is also desired to provide a safe method for hard surface disinfection. Compared to synchronous light, intermittent lighting exposure can significantly reduce inflammatory reaction of the human epidermis. On the other hand, the metabolism of the epidermis can be maintained at a stable level.

Compared to conventional surface disinfection technologies, the disclosed technique develops an asynchronous intermittent lighting system to achieve rapid inactivation for microorganisms including multi-drug-resistant bacteria. The combination of multiple wavelengths and lighting patterns contributes to different inactivation pathways by targeting multiple cellular sites of microorganisms to avoid the possibility of microbial tolerance and resistance. The disclosed surface disinfection technology neither uses chemicals nor damages material surfaces. It is also safe for animals and humans. It is energy-saving, and has the advantage that it can be driven by low-voltage batteries.

The disclosed techniques can be used for surface disinfection of many objects used in laboratory facilities, public infrastructure and household, including, by way of non-limiting examples, biological safety cabinet, medical instruments, handrail, touch panel and bathroom items.

Operation and Implementation

Figure 1B:
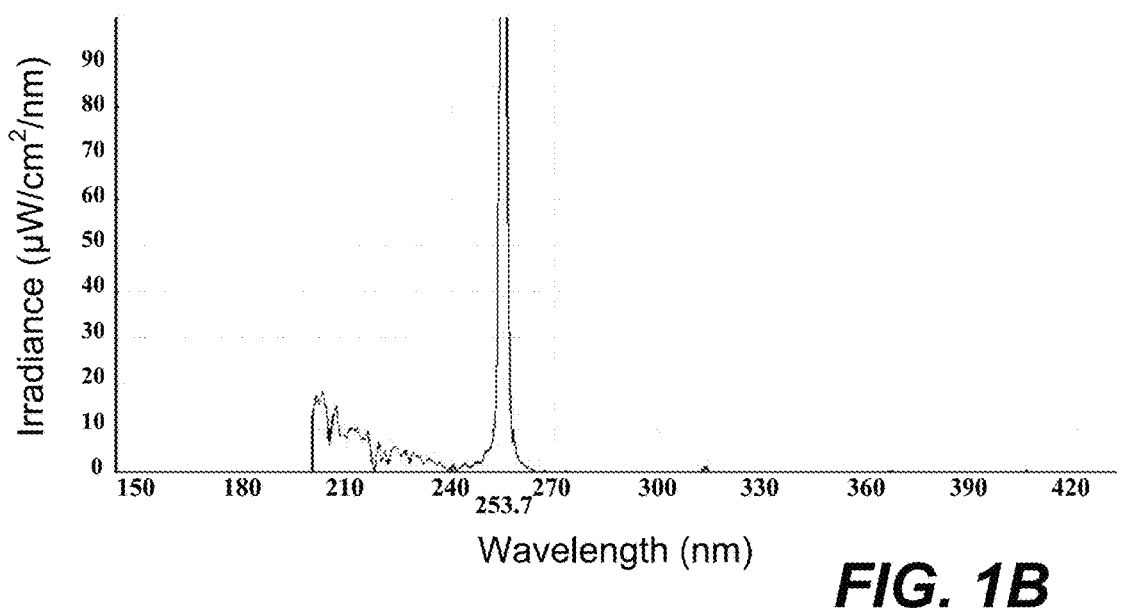
Figure 1C:
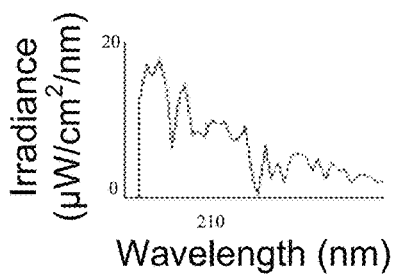
Figure 1D:
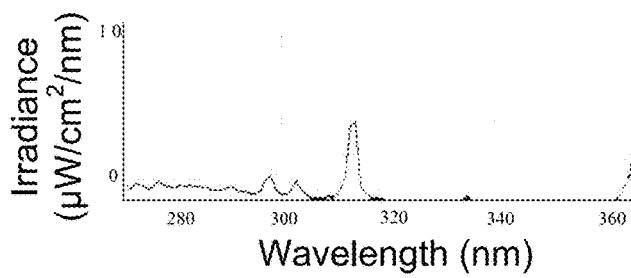

FIGS. 1A-1D are graphic diagrams showing emission spectra of UV (280 nm) LED (FIG. 1A) and UVC fluorescent light (FIGS. 1B-1D). These figures show the emission spectrum of UV LED (SETi, UVTOP270T039FW) with wavelength range within 277±4 nm, and that of UV fluorescent lamp (Phillips, 63872427) showing a broad emission range from 200 to 270 nm with maximum at 253.7 nm. While these are broad emission ranges, for the purposes of the present disclosure, this is considered to be narrow wavelength lighting.

Figure 2A:
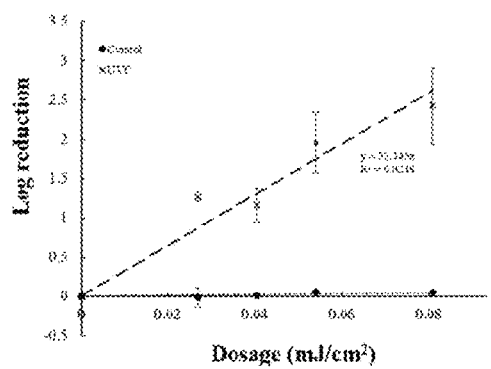
FIGS. 2A-2D are graphic diagrams presenting the bactericidal efficacies of single UV (280 nm) LED against sample bacilli.
Figure 2B:
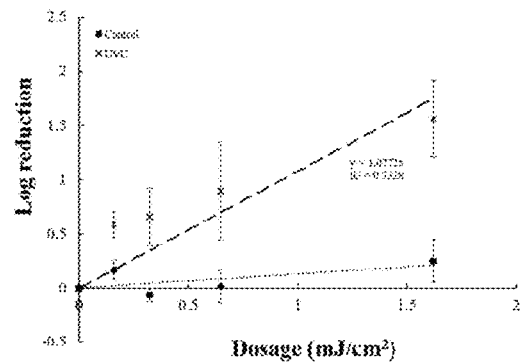
Figure 2C:
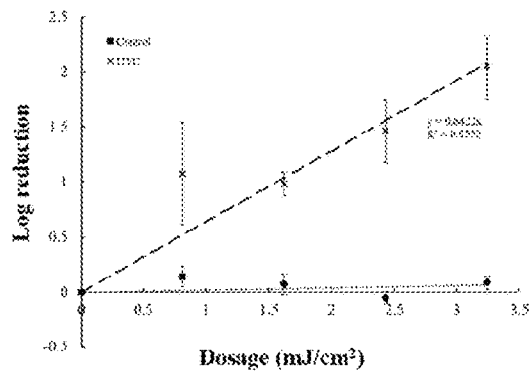
Figure 2D:
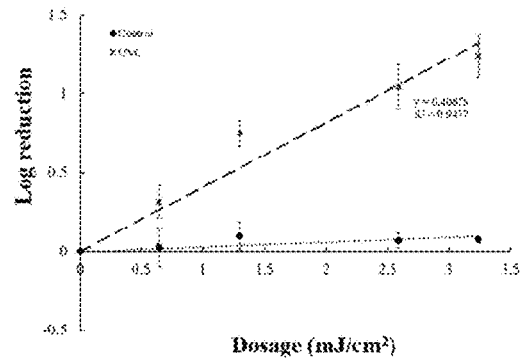

FIGS. 2A-2D are graphic diagrams presenting the bactericidal efficacies of single UV (280 nm) LED against sample bacilli. FIG. 2A samples $P.$ aeruginosa. FIG. 2B samples $E.$ coli. FIG. 2C samples $S.$ aureus. FIG. 2D samples $E.$ faecalis. These figures display the log reduction plots of Gram-positive $S.$ aureus and $E.$ faecalis bacteria and $P.$ aeruginosa is most susceptible to UV LED disinfection followed by $E.$ coli>$S.$ aureus>$E.$ faecalis. It can be seen that a very low light exposure of 2.5 mJ/cm$^2$ can attain better than 90% reduction of $E.$ faecalis, 97% of $S.$ aureus and better than 99.9% of $E.$ coli and $P.$ aeruginosa.

Figure 3A:
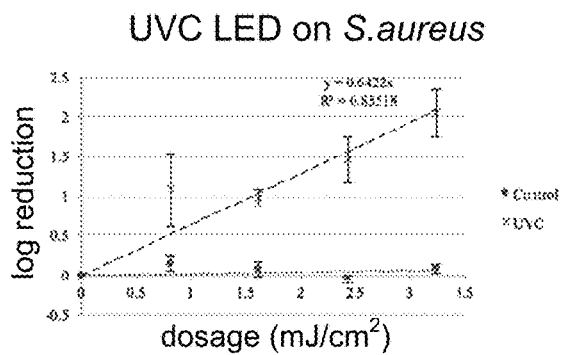
FIGS. 3A and 3B are graphic diagrams showing the bactericidal efficacy against S. aureus.
Figure 3B:
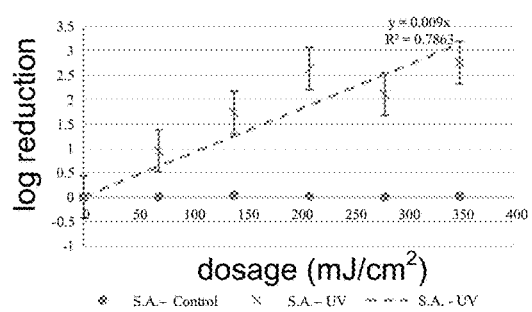

FIGS. 3A and 3B are graphic diagrams showing the bactericidal efficacy against $S.$ aureus. FIG. 3A shows efficacy of UV (280 nm) LED illumination. FIG. 3B shows efficacy of UVC fluorescent light illumination (FIG. 3B). Table 1 summarizes the bactericidal efficacy of UV (280 nm) LED against $P.$ aeruginosa, $E.$ coli, $S.$ aureus and $E.$ faecalis, as plotted in FIG. 3. The table lists that light exposure dosage required for one-log and two-log reductions of $P.$ aeruginosa, $E.$ coli, $S.$ aureus and $E.$ faecalis. A two-log reduction of $P.$ aeruginosa, requires 0.062 mJ/cm$^{-2}$ and $E.$ coli 1.86 mJ·cm$^{-2}$. The Gram-positive bacteria were more resistant to UV with $S.$ aureus and $E.$ faecalis requiring 2.45 mJ/cm$^{-2}$ for one-log reduction. The k-value from Chick's equation is also listed in the table and provides a quantitative comparison of the relative disinfection rate of UV LED for the different bacteria.

TABLE 1

| Bactericidal activity of UV LED for Gram-positive and Gram-negative bacteria | | | | |
|---|---|---|---|---|
| Dosage | Gram-negative | | Gram-positive | |
| (mJ/cm$^2$) | $P.$ aeruginosa | $E.$ coli | $S.$ aureus | $E.$ faecalis |
| 1 log (90% reduction) | 0.03 | 0.93 | 1.56 | 2.45 |
| 2 log (99% reduction) | 0.062 | 1.86 | 3.11 | >3.1 |
| k value from Chick's equation | 74.48 | 2.62 | 1.59 | 0.94 |

FIGS. 3A and 3B compare the bactericidal performance of the fluorescent UV to UV LED in the disinfection of 10$^4$ CFU.ml$^{-1}$ $S.$ aureus. It can be seen from the log reduction plots of viable $S.$ aureus bacteria that UV LED attain log 2 reduction (99%) reduction at a fraction of energy (3.2 mJ/cm$^2$) compared to fluorescent UV lamp (ca. 215 mJ/cm$^2$) even though the latter emits more energetic UV (254 nm).

Figure 4:
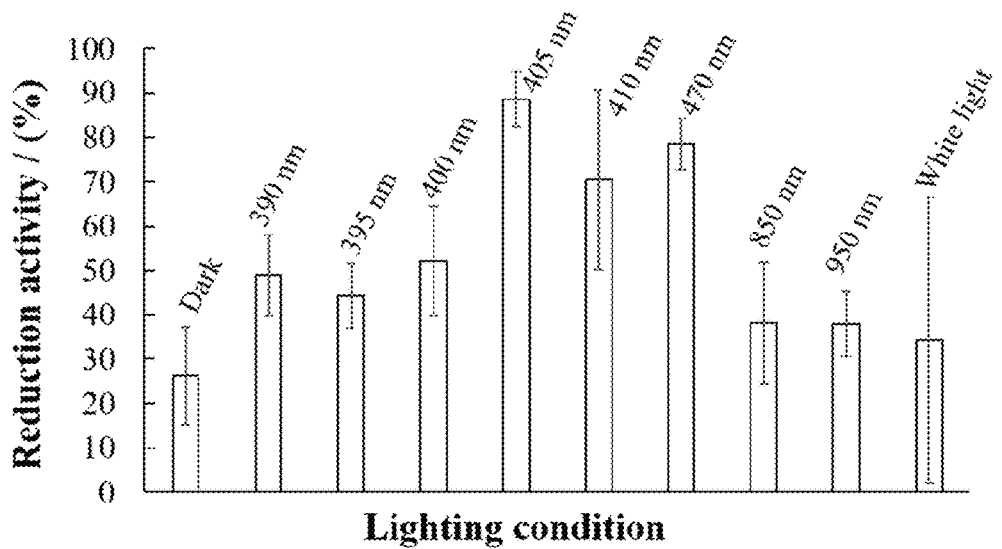
FIG. 4 is a graphic diagram showing bactericidal activities of different lighting (i.e., wavelengths) to $10^4$ CFU/ml, vs. efficacy against E. coli.

FIG. 4 is a graphic diagram showing bactericidal activities of different lightings (i.e., wavelengths) to 10$^4$ CFU/ml, vs. efficacy against $E.$ coli. Table 2 summarizes the performance UV (280 nm) LED and UVC fluorescent light for inactivation of $S.$ aureus and $E.$ faecalis.

Table 2 addresses the performance of the two types of UV light for inactivation of the sample gram-positive bacteria ($S.$ aureus and $E.$ faecalis). It was observed that UV LED requires less light exposure dosage (i.e., 1/10) compared to fluorescent UV to attain the same level of bacteria inactivation. The difference is also reflected by the k-values of the Chick's equation where the k-value of UV LED lights being 80 times higher.

TABLE 2

Bactericidal activity of UV LED and fluorescent UV for Gram-positive bacteria

|  | Single UV(280 nm) LED (intensity: 5.402 μW/cm$^2$) | | UV fluorescent lamp (intensity: 300 μW/cm$^2$ at 5 cm) | | Differences between two light sources |
| --- | --- | --- | --- | --- | --- |
|  | S. aureus | E. faecalis | S. aureus | E. faecalis |  |
| 1 log (90%) | 1.56 mJ/cm$^2$ | 2.45 mJ/cm$^2$ | 111 mJ/cm$^2$ | 222 mJ/cm$^2$ | Dosage requirement: LED < fluorescent by about 10 times |
| 2 log (99% reduction) | 3.11 mJ/cm$^2$ | >3.1 mJ/cm$^2$ | 200 mJ/cm$^2$ | 400 mJ/cm$^2$ |  |
| k value from Chick's equation | 1.59 | 0.94 | 0.021 | 0.012 | LED > fluorescent by about 10 times |

The bactericidal activities of different lightings are shown in FIG. 4 (i.e., wavelengths) to 10$^4$ CFU/ml, vs. efficacy against E. coli. This figure shows a plot of the bactericidal properties of different wavelengths of visible and near infrared lights. The bactericidal experiments were carried out in triplicate on 10$^4$ $^{CFU}$.ml$^{-1}$ E. coli. Under comparable light exposure, 405 nm and 470 nm lighting provide the most consistent disinfection performance. The 405 nm light can achieve 80-85% reduction in viable E. coli, while 470 nm gave 75-80% reduction. Although 410 nm light also has good performance, the results are less consistent compared to 405 and 470 nm lights. The other lightings were only able to attain 50% reduction in E. coli. It is conceivable that other microorganisms may display different susceptibility to different light wavelengths.

Figure 5A:
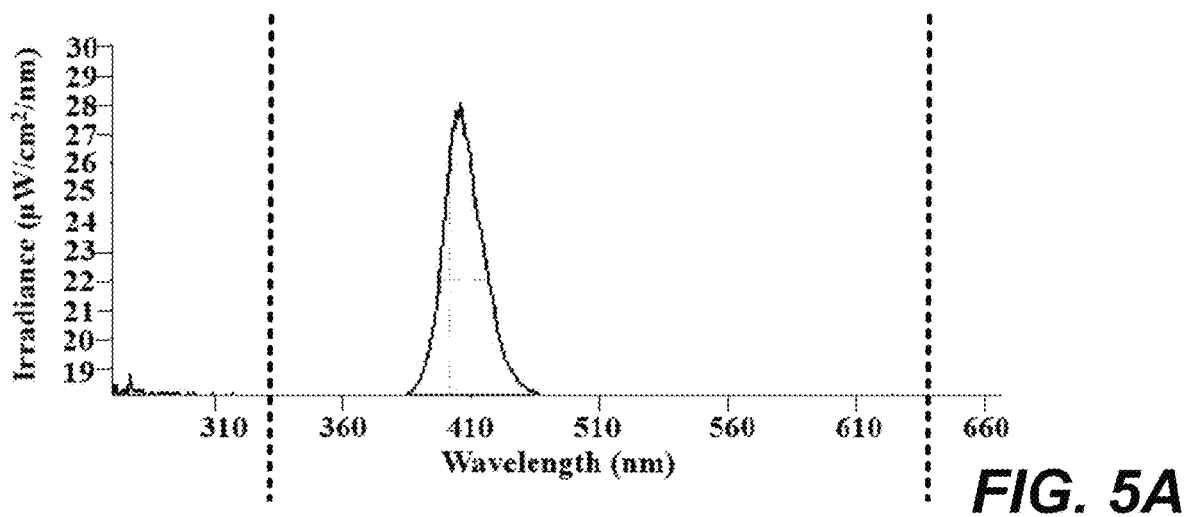
FIGS. 5A and 5B are graphic diagrams showing emission spectra of visible LED lights with the wavelengths of 405 nm (FIG. 5A) and 470 nm (FIG. 5A).
Figure 5B:
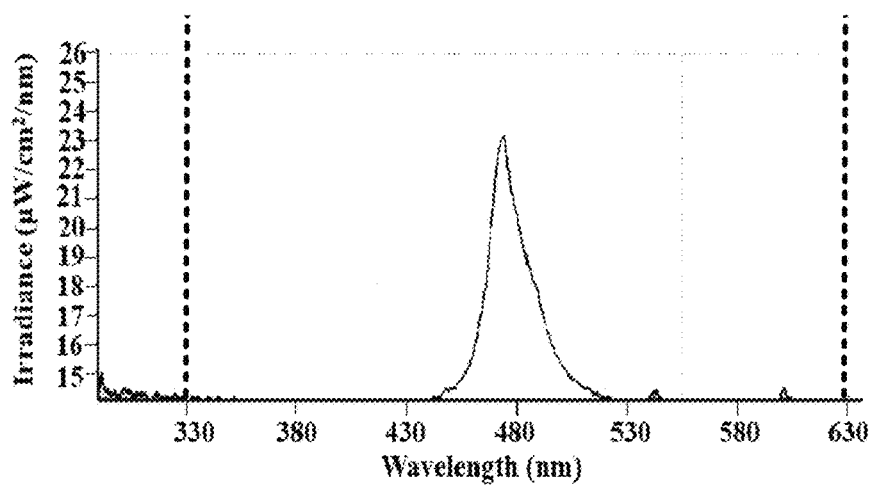

FIGS. 5A and 5B are graphic diagrams showing emission spectra of visible LED lights with the wavelengths of 405 nm (FIG. 5A) and 470 nm (FIG. 5A). These figures show the emission spectrum single 405 nm LED (Bivar, UVSTZ-405015, from Bivar, Inc. of Irvine, Calif.) and single 470 nm LED (Broadcom, HLMP-CB1B-XY0DD, from Broadcom Inc. of Irvine, Calif.).

Table 3 summarizes the bactericidal efficacy of single 405 nm LED and high intensity 405 nm LED against S. aureus. The high intensity 405 nm LED was more effective in inactivating S. aureus with the k-value for the Chick's equation of 0.0031 compared to the low intensity 405 nm LED (k-value=0.0015).

TABLE 3

Bactericidal efficacies of Low and high intensity 405 nm LED for S. aureus

|  | Low Intensity (32 μW/cm$^2$) | High Intensity (569 μW/cm$^2$ at 5 cm) |
| --- | --- | --- |
| K value from Chick's equation | 1.5 × 10$^{-3}$ | 3.1 × 10$^{-3}$ |

Figure 6A:
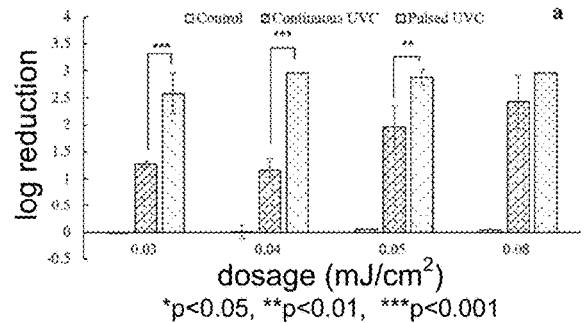
FIGS. 6A-6E are graphic diagrams showing difference between continuous and intermittent (pulsed) UV (280 nm) LED light and their bactericidal efficacies against sample bacilli.
Figure 6B:
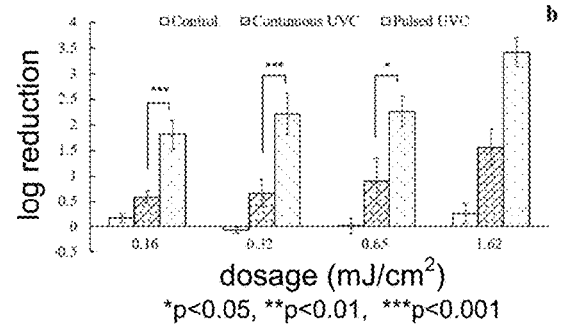
Figure 6C:
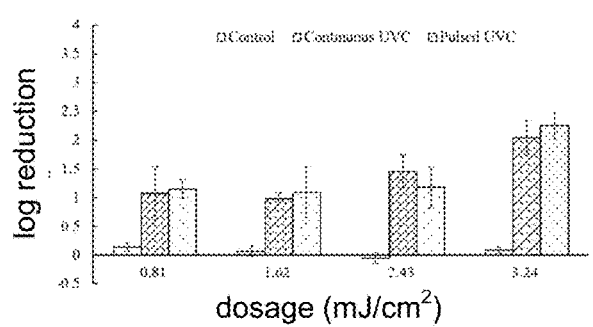
Figure 6D:
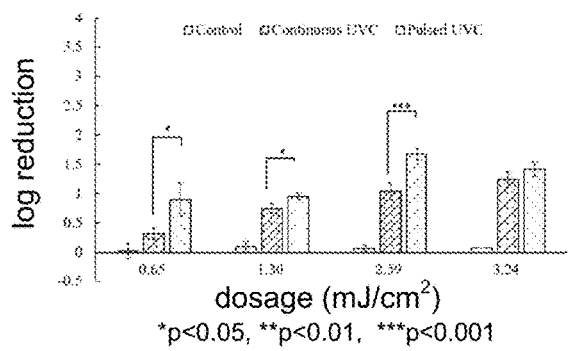
Figure 6E:
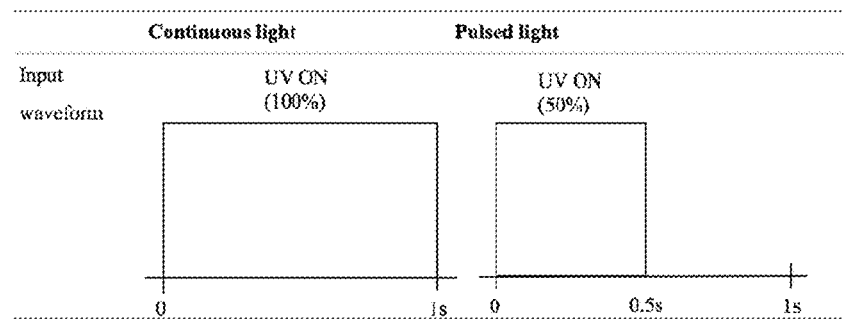

FIGS. 6A-6E are graphic diagrams showing difference between continuous and intermittent (pulsed) UV (280 nm) LED light and their bactericidal efficacies against sample bacilli. FIG. 6A shows efficacy against P. aeruginosa. FIG. 6B shows efficacy against E. coli. FIG. 6C shows efficacy against S. aureus. FIG. 6D shows efficacy against E. faecalis. FIG. 6E shows the applied continuous (100%) and pulsed (50%) waveforms. These figures show that intermittent (pulsed) UV (280 nm) LED light in general has better bactericidal efficacies. Intermittent (pulsed) lighting attained higher microbial inactivation that continuous irradiation for P. aeruginosa, E. coli, and E. faecalis as shown in FIGS. 6A, 6B and 6D. There was less significant difference for S. aureus as the p-values from the t-test were larger than 0.05 (FIG. 6C). FIG. 6A shows that 2.5 log reduction was obtained for P. aeruginosa for intermittent (pulsed) irradiation at a light exposure dosage of 0.027 mJ/cm$^2$ that is only a third of the required dosage when continuous lighting was used. Its effects is particularly pronounced at low light exposure dosage (<0.054mJ/cm$^2$ (p<0.01)). For E. coli, it can be seen in FIG. 6B that intermittent (pulsed) UV (280 nm) LED light achieved better than 1.5 log reduction in one minute at light exposure dosage of 0.16 mJ/cm$^2$, a fraction of that needed when continuous UV (280 nm) LED irradiation was used (i.e., 5 min, 1.62 mJ/cm$^2$). Similar observations but with less pronounced effects can be seen from the results for S. aureus and E. faecalis (FIGS. 6C and 6D).

Figure 7:
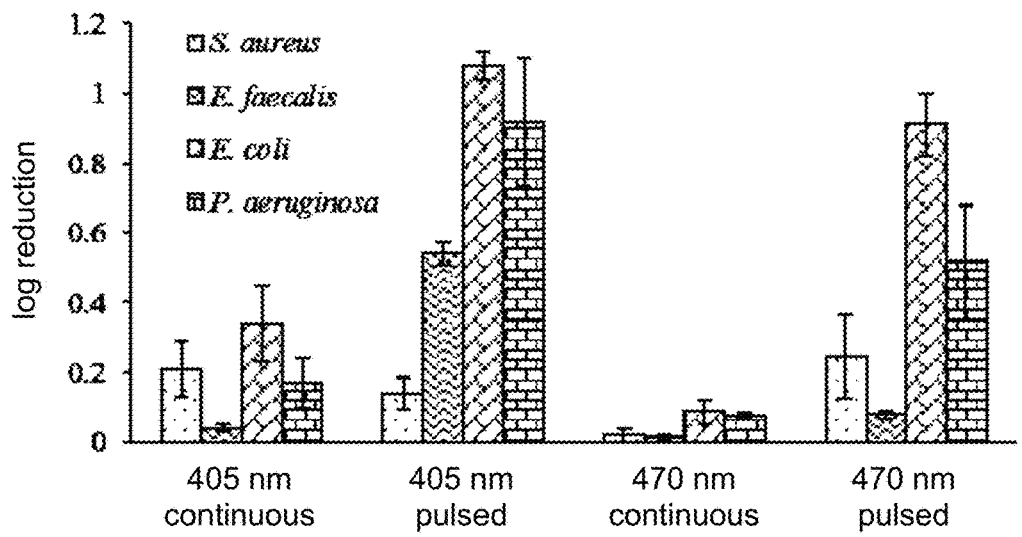
FIG. 7 is a graphic diagram showing difference in the bactericidal efficacies of continuous and intermittent (pulsed) blue LED lights with the wavelengths of 405 nm and 470 nm against P. aeruginosa, E. coli, S. aureus and E. faecalis.

FIG. 7 is a graphic diagram showing difference in the bactericidal efficacies of continuous and intermittent (pulsed) blue LED lights with the wavelengths of 405 nm and 470 nm against P. aeruginosa, E. coli, S. aureus and E. faecalis. This figure shows that intermittent (pulsed) lighting has the effects of enhancing the bactericidal activities of 405 nm and 470 nm LED lights. Intermitted pulsed 405 nm LED shows significant increase in log-reduction of viable P. aeruginosa, E. coli and E. faecalis, while intermittent pulsed 470 nm LED shows higher reduction for all four bacteria.

Figure 8A:
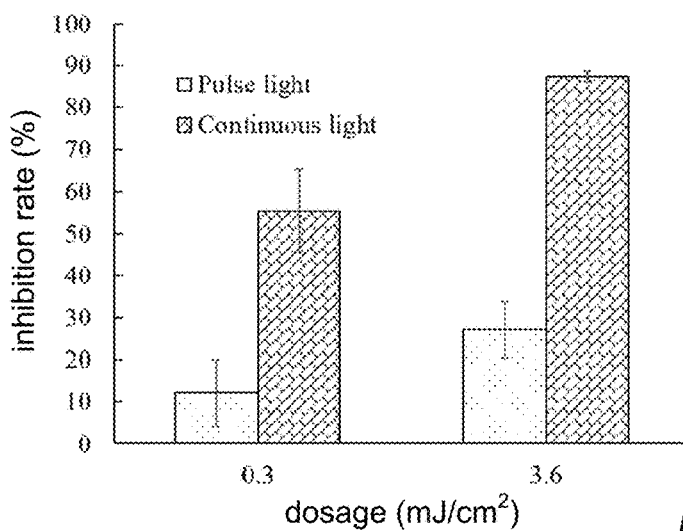
FIGS. 8A and 8B are graphic diagrams showing cytotoxicity against A431 cells (human epidermis squamous carcinoma) of continuous and intermittent (pulsed) light.
Figure 8B:
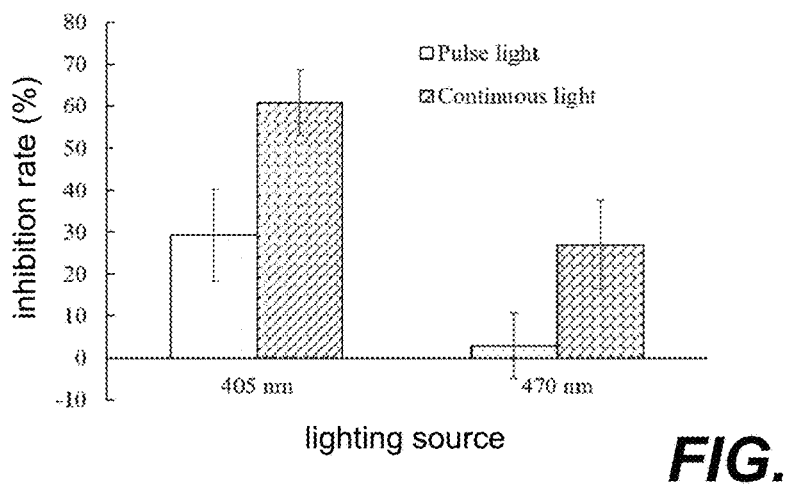

FIGS. 8A and 8B are graphic diagrams showing cytotoxicity against A431 cells (human epidermis squamous carcinoma) of continuous and intermittent (pulsed) light. FIG. 8A shows cytotoxicity at different dosages for UV (280 nm) light. FIG. 8B shows cytotoxicity for 405 nm and 470 nm blue lights. These figures display the MTT assay on A431 human epidermis cells (squamous carcinoma) following exposure to intermittent (pulsed) and continuous lighting. It is evident in FIG. 8A that intermittent (pulsed) UV (280 nm) LED lighting has lower inhibition rate (e.g., safer) than continuous irradiation at low (0.3 mJ/cm$^2$) and high (3.6 mJ/cm$^2$) light exposure dosages. At 0.3mJ/cm$^2$, more than half of the cells were inhibited by continuous light but only 10% were inhibited by intermittent (pulsed) lighting. A large portion (80%) of the cells were inhibited by continuous light at 3.6mJ/cm$^2$ UV (280 nm) LED light exposure dosage compared to less than 30% inhibition rate for intermittent (pulsed) lighting. The results indicate that intermittent (pulsed) UV (280 nm) LED is safer than continuous irradiation under the same light exposure dosages. Similar observations were made for 405 nm and 470 nm LED lights (FIG. 8B) with intermittent (pulsed) lighting causing less cell inhibition. The intermittent 405 nm and 470 nm LED lights decreases cell inhibition by half and ninety percent compared to continuous lighting. Again, this shows that the intermittent (pulsed) lighting are safer.

Figure 9:
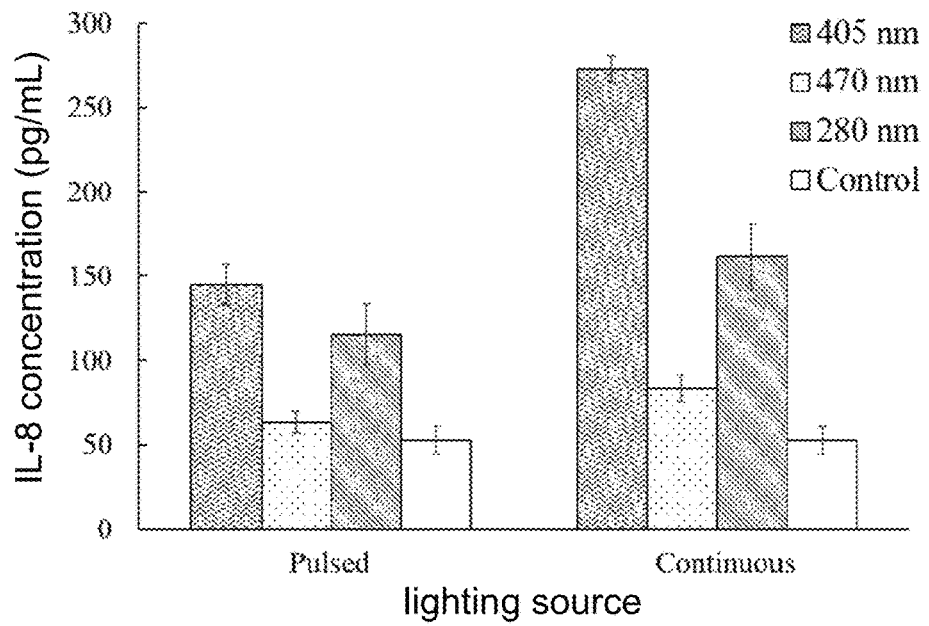
FIG. 9 is a graphic diagram showing human IL-8 level of A431 cells after irradiation by pulsed and continuous light at different frequencies. The left side shows the effect of pulsed light, and the right side shows the effect of continuous light.

FIG. 9 is a graphic diagram showing human IL-8 level of A431 cells after irradiation by pulsed and continuous light at different frequencies. The left side shows the effect of pulsed light, and the right side shows the effect of continuous light. This figure displays the results of human IL-8 ELISA assay on the A431 human epidermis cells (squamous carcinoma) following exposure to intermittent (pulsed) and continuous lighting. IL-8 is a key mediator associated with inflammation and plays a causative role in acute inflammation by recruiting and activating neutrophils. Thus, the level of IL-8 is an indicator of inflammatory response. FIG. 9 shows intermittent (pulsed) lighting generally have lower levels of IL-8 compared to continuous lighting. The difference is remarkable for 405 nm LED lights.

Figure 10A:
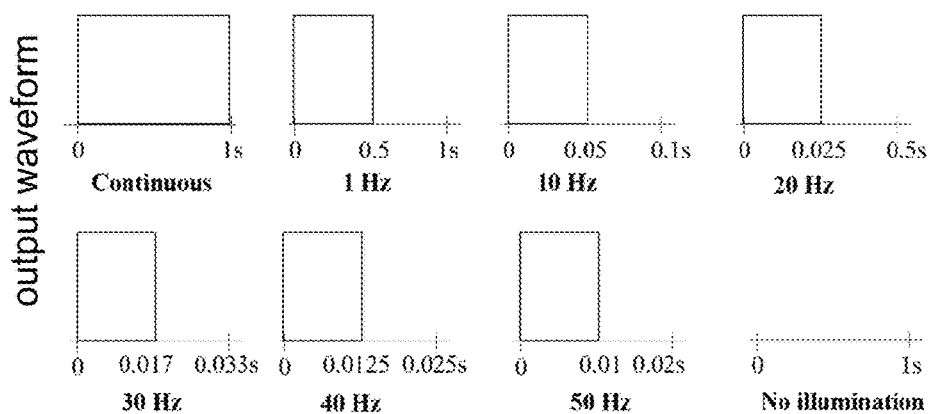
FIGS. 10A-10E are graphic diagrams showing a comparison between the bactericidal efficacies of UV (280 nm) LED at different rates of continuous and intermittent (pulsed) lighting against sample bacilli.
Figure 10B:
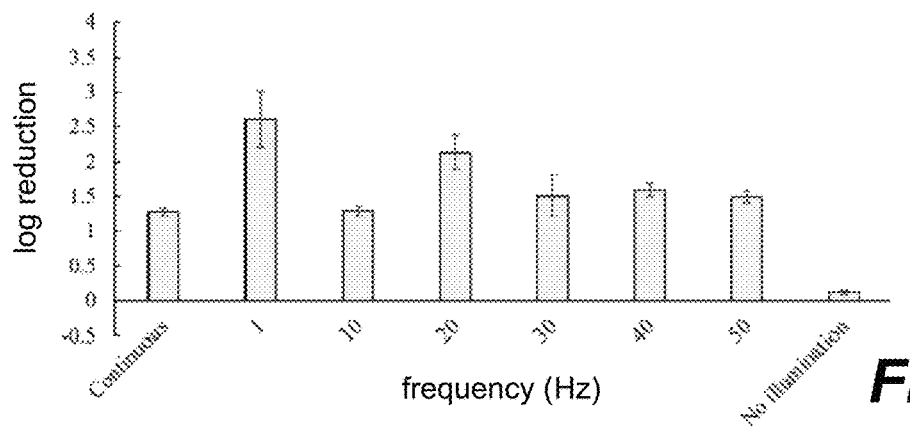
Figure 10C:
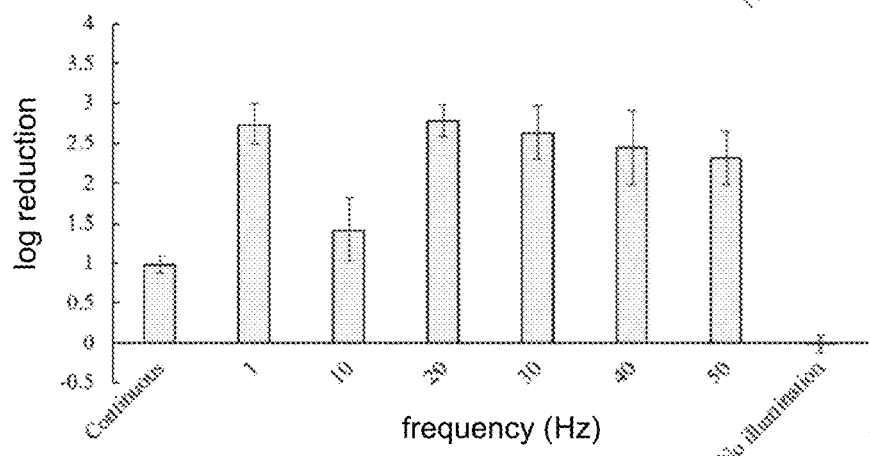
Figure 10D:
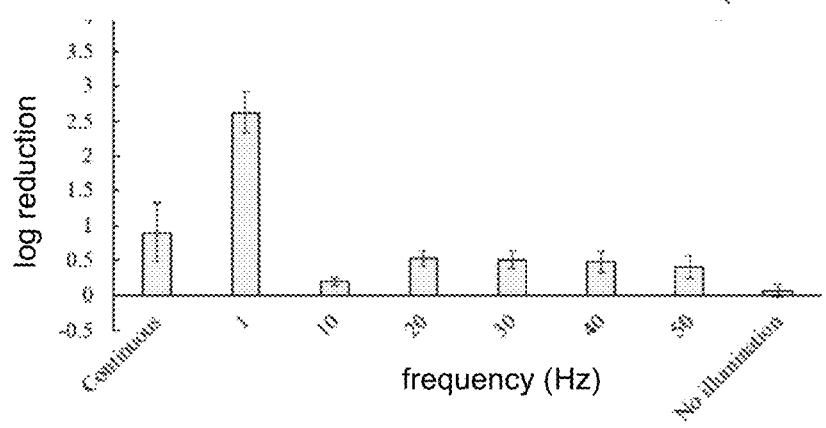
Figure 10E:
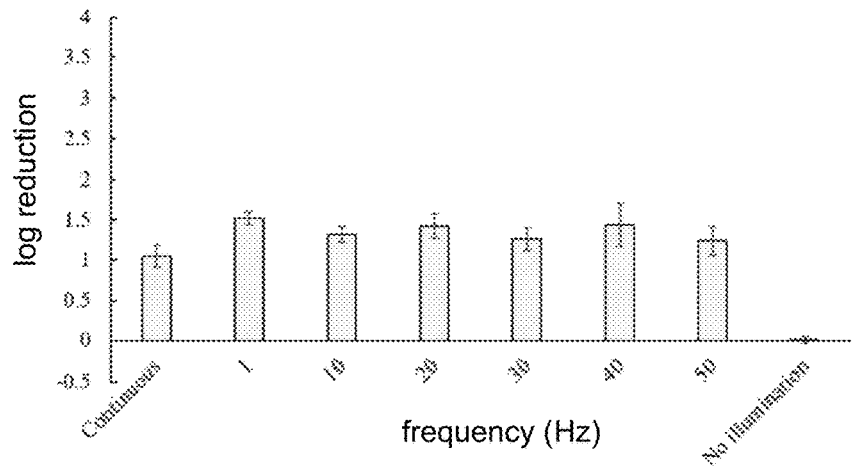

FIGS. 10A-10E are graphic diagrams showing a comparison between the bactericidal efficacies of UV (280 nm) LED at different rates of continuous and intermittent (pulsed) lighting against sample bacilli. FIG. 10A shows the illumination frequencies. FIG. 10B samples P. aeruginosa. FIG. 10C samples E. coli. FIG. 10D samples S. aureus. FIG. 10E samples E. faecalis. FIG. 10C-10 shows the applied waveforms. These figures compare the bactericidal efficacies of UV (280 nm) LED at intermittent (pulsed) lighting of 1, 10, 20, 30, 40 and 50 Hz. The result shows that the best performance is obtained at 1 Hz for all four tested bacteria. The 1 Hz intermittent (pulsed) lighting has significantly higher reduction of viable P. aeruginosa than 10, 30, 40 and 50 Hz ($p<0.001$). FIG. 10A shows the lighting rates. The same could be said for E. coli and S. aureus where 1 Hz intermittent (pulsed) lighting also led to significantly higher bactericidal efficacy than all other frequencies ($p<0.001$). E. faecalis reduction is less sensitive to the pulsing rate of the UV (280 nm) LED light.

Figure 11A:
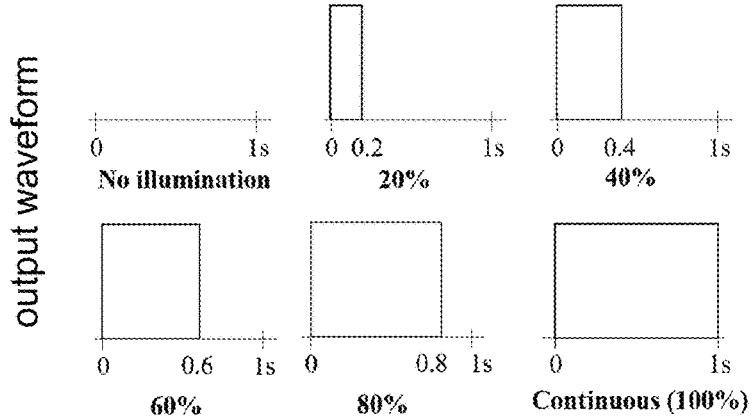
FIGS. 11A-11E are graphic diagrams showing a comparison between the bactericidal efficacies of UV (280 nm) LED at different duty cycles against sample bacilli.
Figure 11B:
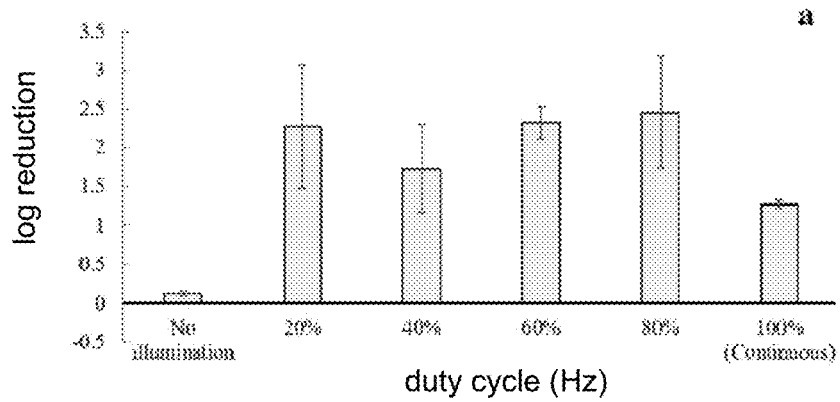
Figure 11C:
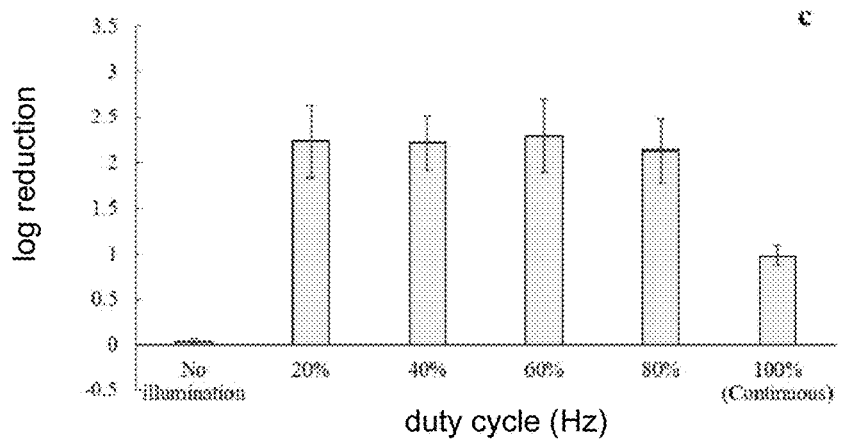
Figure 11D:
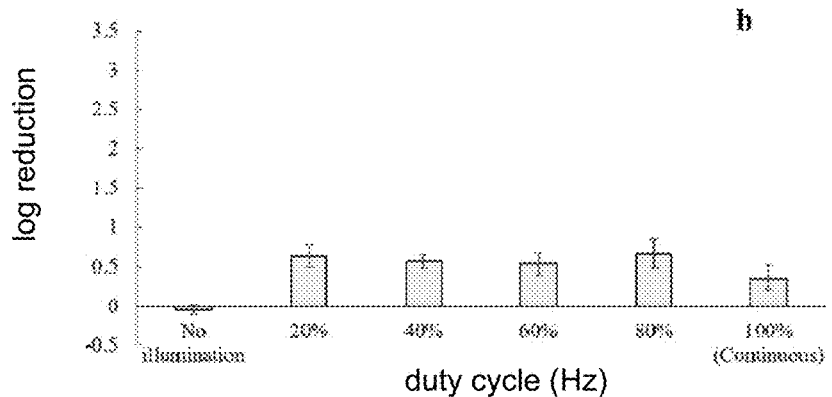
Figure 11E:
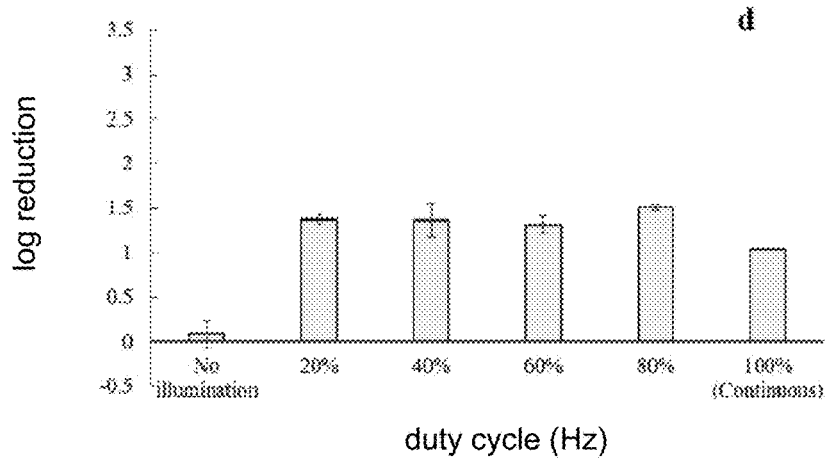

FIGS. 11A-11E are graphic diagrams showing a comparison between the bactericidal efficacies of UV (280 nm) LED at different duty cycles against sample bacilli. FIG. 11A shows the duty cycles of the applied waveforms. FIG. 11B samples P. aeruginosa. FIG. 11C samples E. coli. FIG. 11D samples S. aureus. FIG. 11E samples E. faecalis. These figures show the bactericidal effect of pulsed light at various duty cycle (0, 20, 40, 60, 80, and 100%). The reduction of viable P. aeruginosa, E. coli, S. aureus and E. faecali bacteria is less insensitive to the duty cycle with $p>0.05$ compared to the rate of intermittent (pulsed) lighting.

Figure 12:
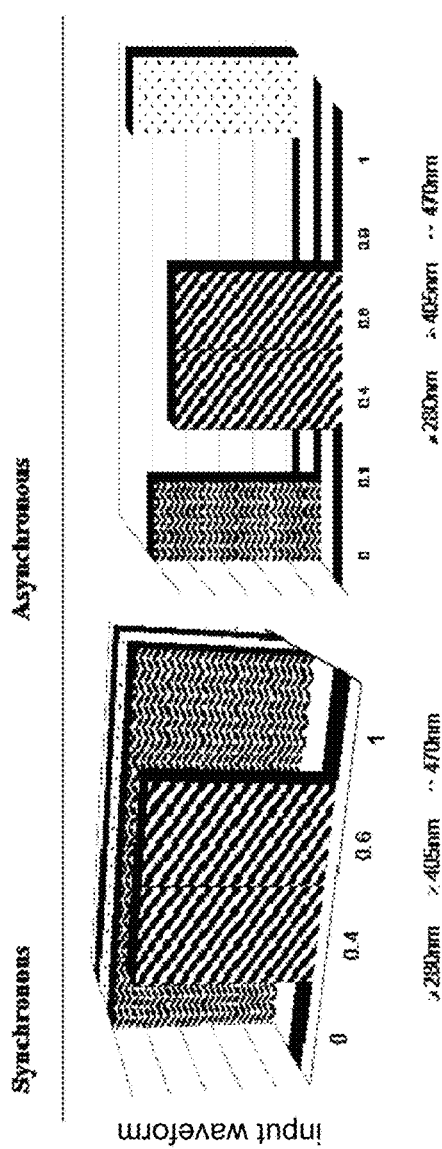
FIG. 12 is a set of graphic diagrams comparing synchronous and asynchronous lightings.

FIG. 12 is a set of graphic diagrams comparing synchronous and asynchronous lighting. These depictions show the waveform of the synchronous and asynchronous lighting patterns. A synchronous lighting pattern occurs when lights of different wavelengths were illuminated at the same time within the same duty cycle as shown in the figure. The asynchronous lighting pattern is when one or more sets of lights are illuminated in a way that they do not overlap with each other as shown in an example in the figure. The example of synchronous light as shown in the figure is the continuous blue lights (405 nm and 470 nm) with 1 Hz pulsed UV, and the example of asynchronous light in the figure is the alternating pulsing of UV (280 nm), 405 nm and 470 nm LED lights. In the continuous and asynchronous examples, 10 W LEDs are used.

In applying the synchronous waveform, as depicted on the left side of FIG. 12, continuous lighting from 405 nm and 470 nm is applied. Pulsed UV light from four 280 nm LEDs is applied, operating at 1 Hz and a 20% duty cycle. Asynchronous light is applied, as depicted on the right side as pulsed 405 nm and 470 nm lighting at 1 Hz and a 10% duty cycle. Pulsed UV light from four 280 nm LEDs is applied, operating at 1 Hz and a 20% duty cycle. In the asynchronous application, the light was pulsed alternately.

Figure 13:
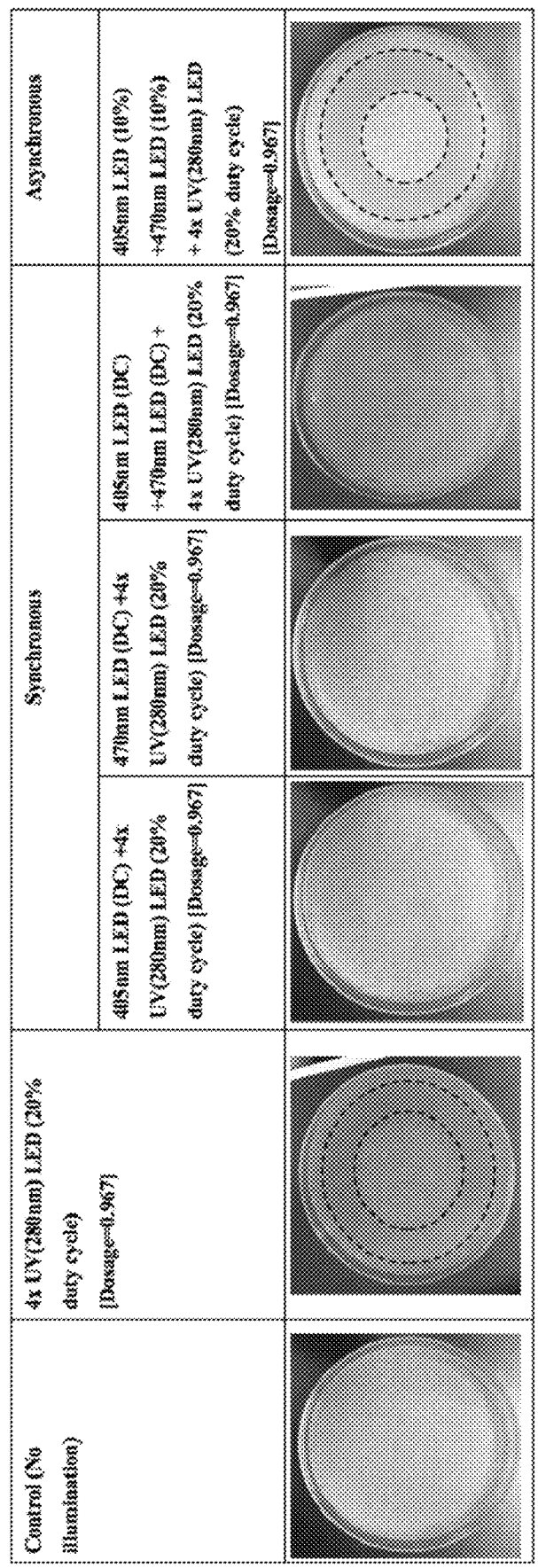
FIG. 13 is a comparative grouped array of photographic depictions of petri dishes showing bactericidal efficacy of synchronous and asynchronous lighting. The depictions are, from left to right, a control sample; a sample running a 20% duty cycle; three samples subject to synchronous light exposure; and a sample subject to asynchronous light exposure.

FIG. 13 is a comparative grouped array of photographic depictions of petri dishes showing bactericidal efficacy of synchronous and asynchronous lighting. The depictions are, from left to right, a control sample; a sample running a 20% duty cycle; three samples subject to synchronous light exposure; and a sample subject to asynchronous light exposure. The petri dishes show the bactericidal efficacies of intermittent (pulsed) UV (280 nm) LED light, synchronous (concurrent 405 nm and UV as well as concurrent 470 nm and UV) and asynchronous lighting patterns. The bacteria on culture plate exposed to intermittent (pulsed) UV (280 nm) LED light serves as reference for bactericidal efficacy of the UV component of the lighting system. A clear track on the plates indicates the bactericidal efficacy. No clear track can be observed from asynchronous lighting indicating poor bactericidal efficacies despite the presence of the same UV (280) LED light. The asynchronous lighting on the other hand created a wider clearance track compared to UV (280 nm) LED light indicating greater bactericidal efficacy. The poorer performance of synchronous lighting is due to healing effect of 405 nm lights on damaged DNA/RNA.

Figure 14:
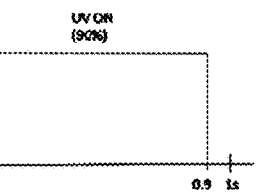
FIG. 14 is a depiction of a set of waveforms of different lighting combinations for microbial disinfection exposures.
Figure 14:
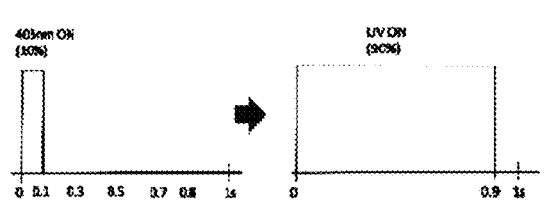
Figure 14:
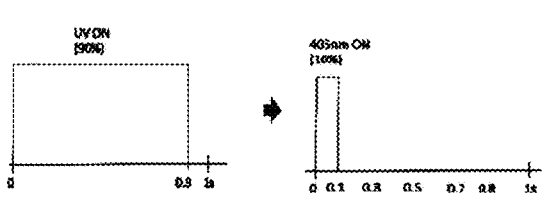
Figure 14:
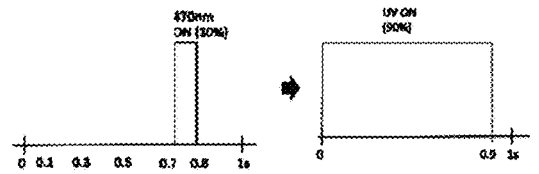
Figure 14:
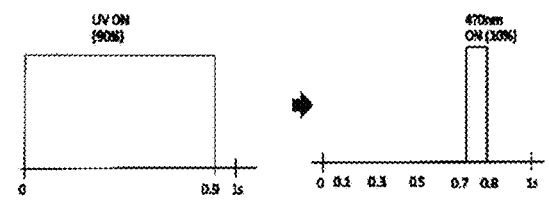
Figure 14:
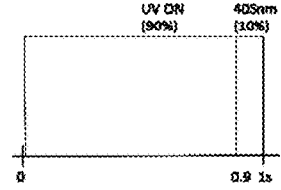
Figure 14:
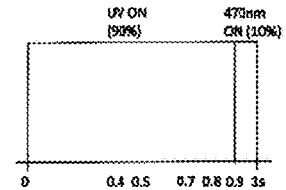

FIG. 14 is a depiction of a set of waveforms of different lighting combinations for microbial disinfection exposures. These waveforms show the lighting schemes investigated to determine the optimum lighting for best bactericidal efficacy. This includes UV-only exposure, pre- and post-exposure of blue light (405 nm or 470 nm) to UV and alternative exposure of blue light (405 nm or 470 nm) with UV.

Figure 15A:
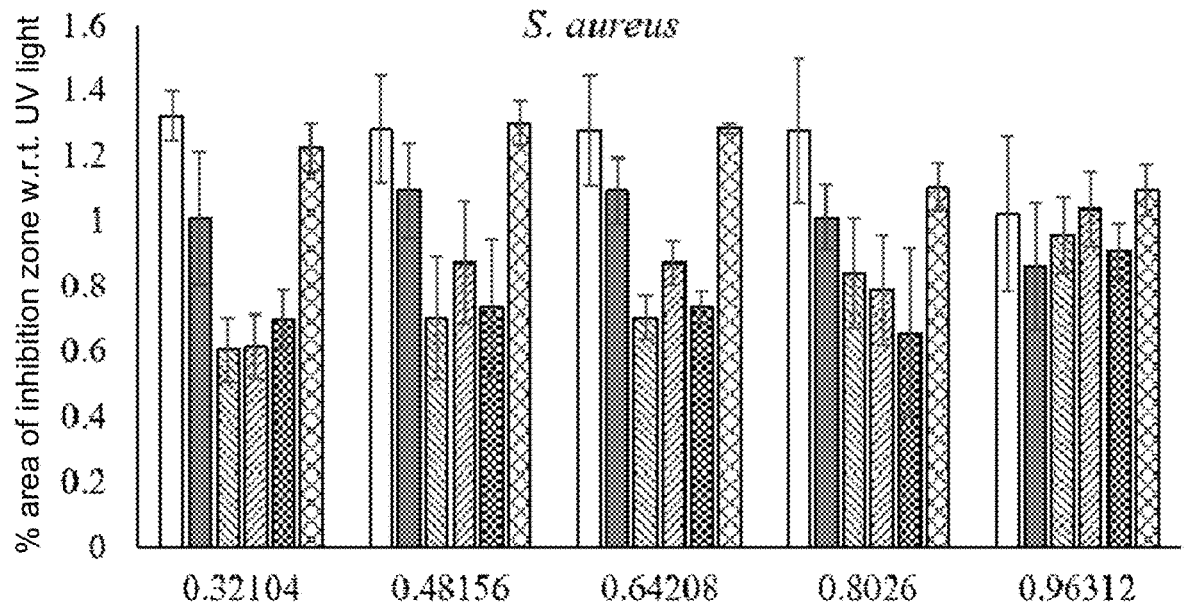
FIGS. 15A and 15B are graphic diagrams showing a comparison between the bactericidal performance of different lighting combinations compared to UV LED against sample bacilli.
Figure 15B:
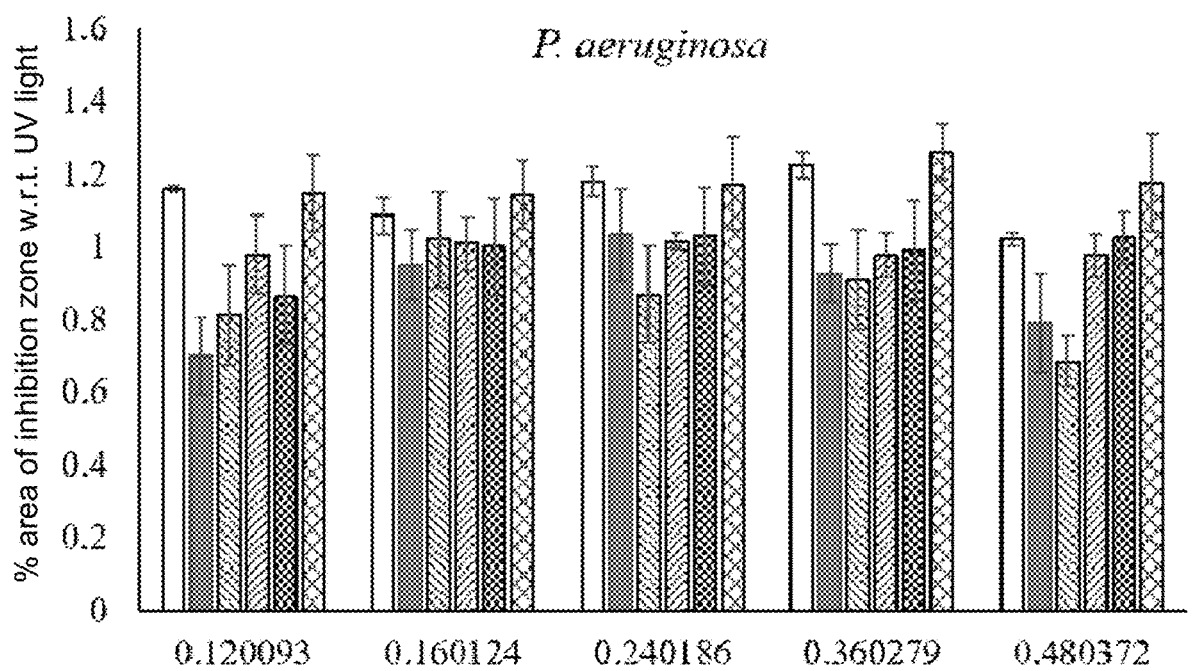

FIGS. 15A and 15B are graphic diagrams showing a comparison between the bactericidal performance of different lighting combinations compared to UV LED against sample bacilli. FIG. 15A samples S. aureus. FIG. 15b samples P. aeruginosa. These figures show the bactericidal efficacies of the lighting schemes illustrated in FIG. 14. The bactericidal efficacies were quantified by:

$$\text{Bactericidal performance} = \frac{\% \text{ Area of inhinbtion zone caused by light combination}}{\% \text{ Area of inhibition zone caused solely by } UV \text{ light}}$$

A value of 1 would indicate similar bactericidal efficacy as UV light. A larger value would mean improvement while a smaller value would mean diminished bactericidal efficacy compared to UV light alone.

Table 4 summarizes the comparison among bactericidal effect of different lighting combinations in FIGS. 14 and 15. The result shows that asynchronous light had to be applied in specific sequence in order to achieve enhancement on bactericidal efficacy. Pre-exposure to 405 nm and alternative exposure to 470 nm could enhance the bactericidal efficacy.

TABLE 4

Bactericidal performance of various lighting scheme as compared to intermittent (pulsed) UV (280 nm) light alone.

| | Pre-exposure to 405 nm | Post-exposure to 405 nm | Pre-exposure to 470 nm | Post-exposure to 470 nm | Alternative exposure to 405 nm | Alternative exposure to 470 nm |
|---|---|---|---|---|---|---|
| P. aeruginosa | Increase 2% to 20% | Decrease 5%-30% | Decrease 10%-30% | Same as UV only exposure | Same as UV only exposure | Increase 12%-26% |
| S. aureus | Increase 10%-30% | Same as UV only exposure | Decrease 5%-40% | Decrease 15%-40%* | Decrease 30%* | Increase 10%-30% |

*Except that no reduction was observed when exposure time was 120 s

Figure 16A:
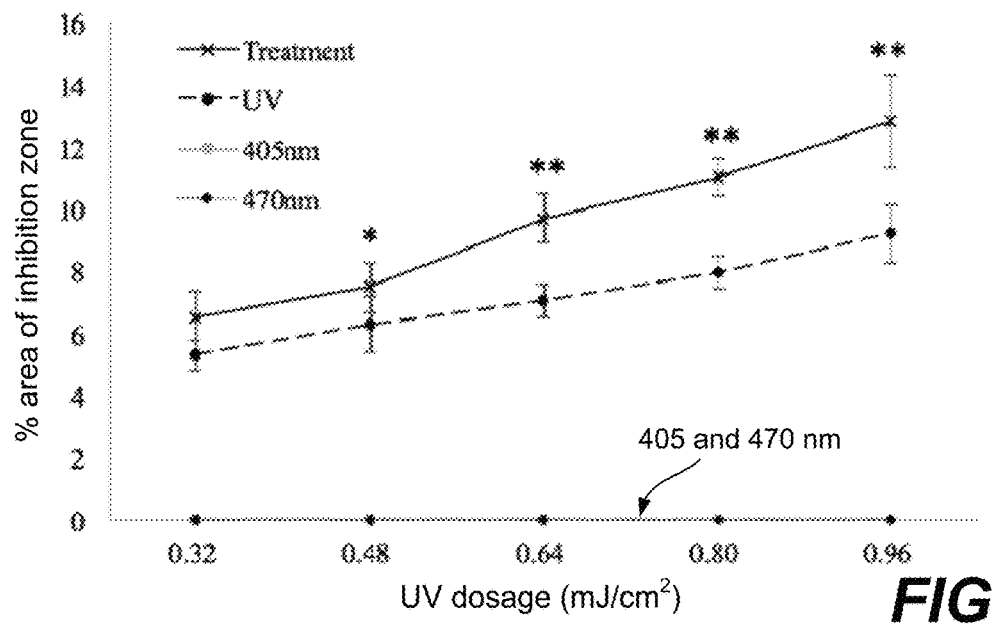
FIGS. 16A and 16B are graphic diagrams showing the optimized asynchronous intermittent disinfection lighting scheme and its bactericidal efficacies as compared to individual component lights (UV (280 nm) LED, 405 nm and 470 nm LEDs) against the optimized asynchronous intermittent disinfection lighting scheme and its bactericidal efficacies as compared to individual component lights.
Figure 16B:
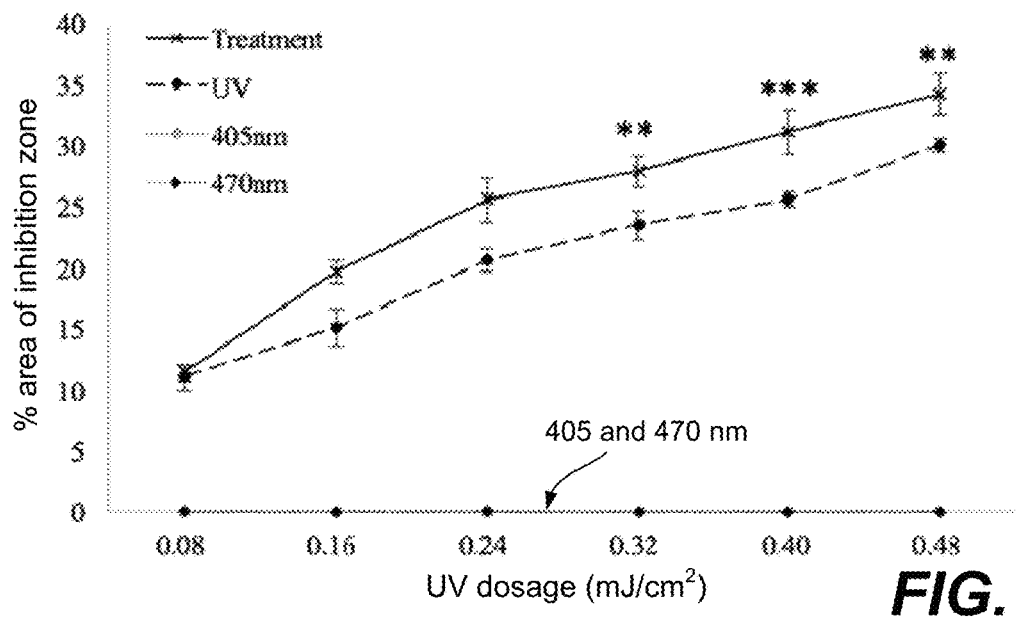
Figure 16C:
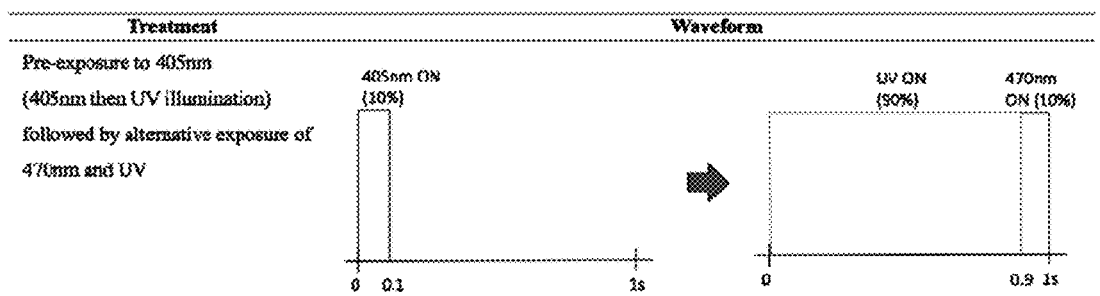
FIG. 16C shows the applied waveforms.

FIGS. 16A-16C show the effects of optimized asynchronous intermittent disinfection lighting. FIGS. 16A and 16B are graphic diagrams showing the optimized asynchronous intermittent disinfection lighting scheme and its bactericidal efficacies against *P. aeruginosa* and *S. aureus* as compared to individual component lights (UV (280 nm) LED, 405 nm and 470 nm LEDs against the optimized asynchronous intermittent disinfection lighting scheme and its bactericidal efficacies as compared to individual component lights. It is noted that no measurable inhibition zones can be observed when single 405 nm and 470 nm LEDs were used for either *P. aeruginosa* or *S. aureus* within the depicted dosage range. FIG. 16C shows the applied waveforms. These figures show the lighting scheme for the optimized asynchronous intermittent light disinfection system comprising two non-overlapping duty cycles of 1 Hz intermittent (pulsed) 405 nm LED lighting (10% duty cycle) followed by 1 Hz intermittent (pulsed) UV (280 nm) LED lighting (90% duty cycle) and 1 Hz intermittent (pulsed) 470 nm LED lighting (10% duty cycle).

FIGS. 16A and 16B present measurements of the areas of the inhibition zone on *P. aeruginosa* and *S. aureus* culture plates from the optimized asynchronous intermittent disinfection light and that of the individual component lights (UV (280 nm) LED, 405 nm and 470 nm LEDs) under identical intermittent (pulsed) rate and duty cycle. The higher bactericidal efficacies for the optimized asynchronous intermittent light disinfection system are evidence of the synergistic effects of the light disinfection system. The bactericidal tests on blue light LEDs by themselves have low bacteria reduction, but exert significantly higher bactericidal effects in the asynchronous lighting system.

Figure 17:
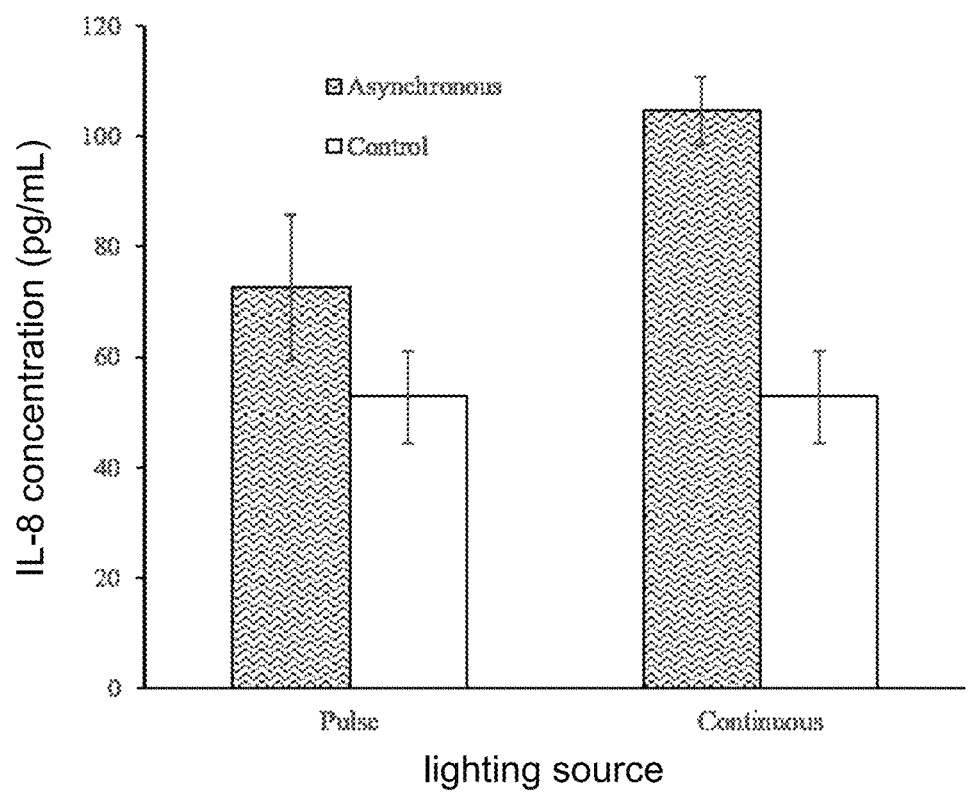
FIG. 17 is a graphic diagram showing human IL-8 level of A431 cells following irradiation by pulsed and asynchronous continuous lighting.

FIG. 17 is a graphic diagram showing human IL-8 level of A431 cells following irradiation by pulsed and asynchronous continuous lighting. This figure shows a significant reduction of IL-8 in mixed lighting system compared to UV LED, under both pulse and continuous lights. It indicates less inflammatory response was caused by the mixed lighting disinfection system than UV light.

Figure 18A:
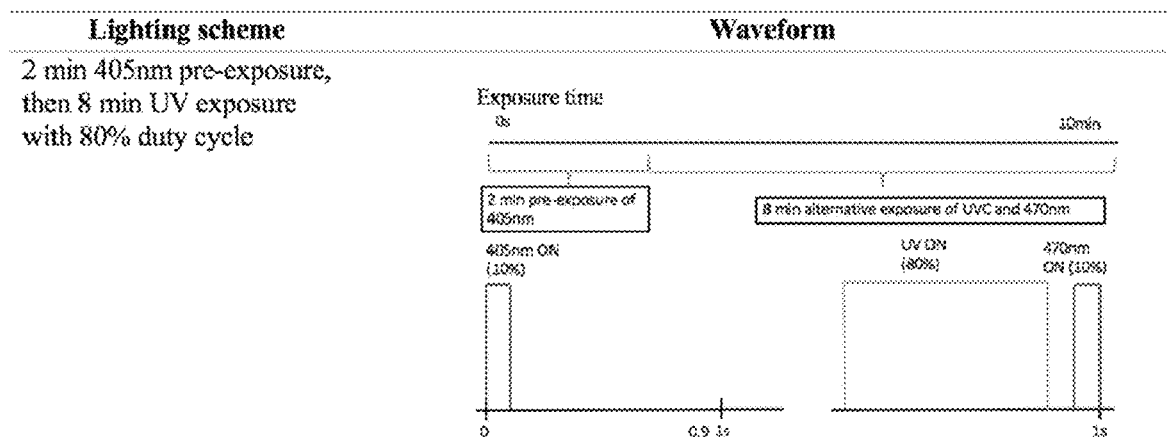
FIGS. 18A, 18B and 18C are graphic diagrams showing the optimized asynchronous intermittent disinfection lighting scheme for inactivation of virus and spore, and its virucidal and sporicidal activities.
Figure 18B:
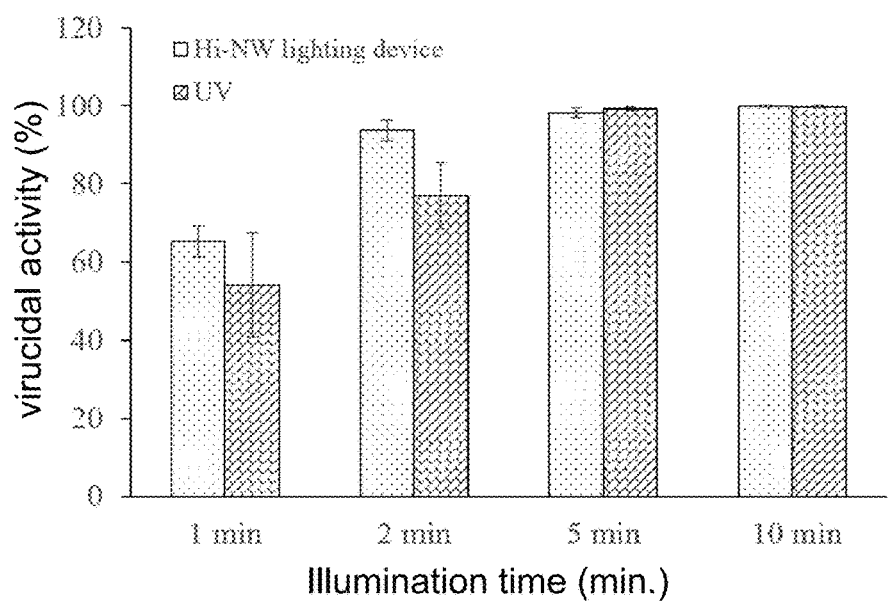
Figure 18C:
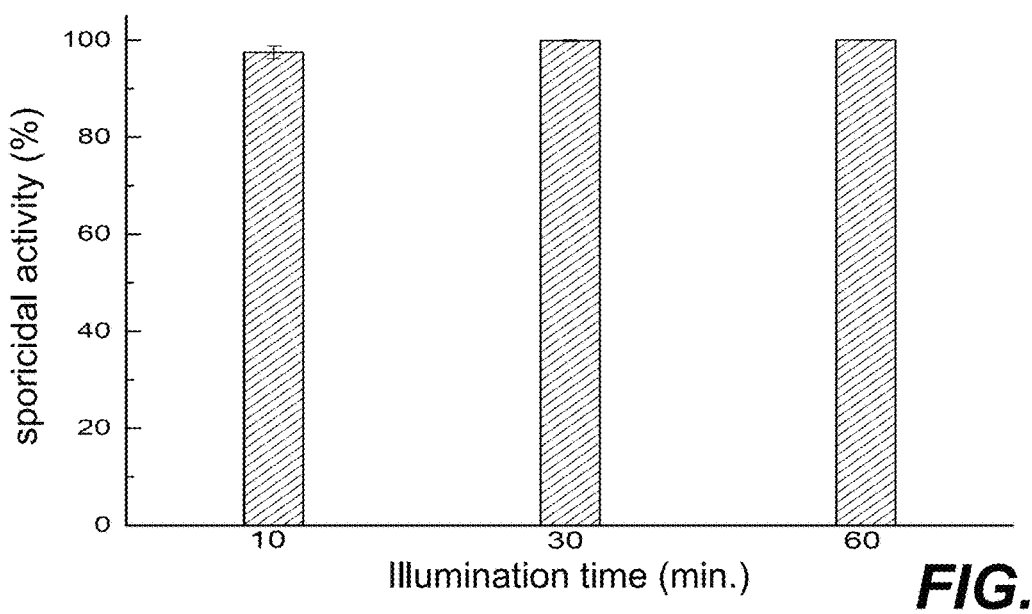

FIGS. 18A, 18B and 18C are graphic diagrams showing the optimized asynchronous intermittent disinfection lighting scheme for inactivation of virus and spore, and its virucidal and sporicidal activities. FIG. 18A shows the waveforms applied against *E. coli* bacteriophage T3. FIGS. 18B and 18C show the virucidal and sporicidal activities against *E. coli* bacteriophage T3 and *Aspergillus niger*, respectively. These figures show the lighting scheme for the optimized asynchronous intermittent light disinfection system comprising two non-overlapping duty cycles of 1 Hz intermittent (pulsed) 405 nm LED lighting (10% duty cycle) during the first 2 min. of the 10 min. exposure time, followed by 1 Hz intermittent (pulsed) UV (280 nm) LED lighting (80% duty cycle) and 1 Hz intermittent (pulsed) 470 nm LED lighting (10% duty cycle) during the remaining 8 min. A dark period between UV (280 nm) LED and 470 nm LED lights was observed to enhance the virucidal activity as compared to intermittent (pulsed) UV (280 nm) LED light exposure alone.

Configuration

Figure 19:
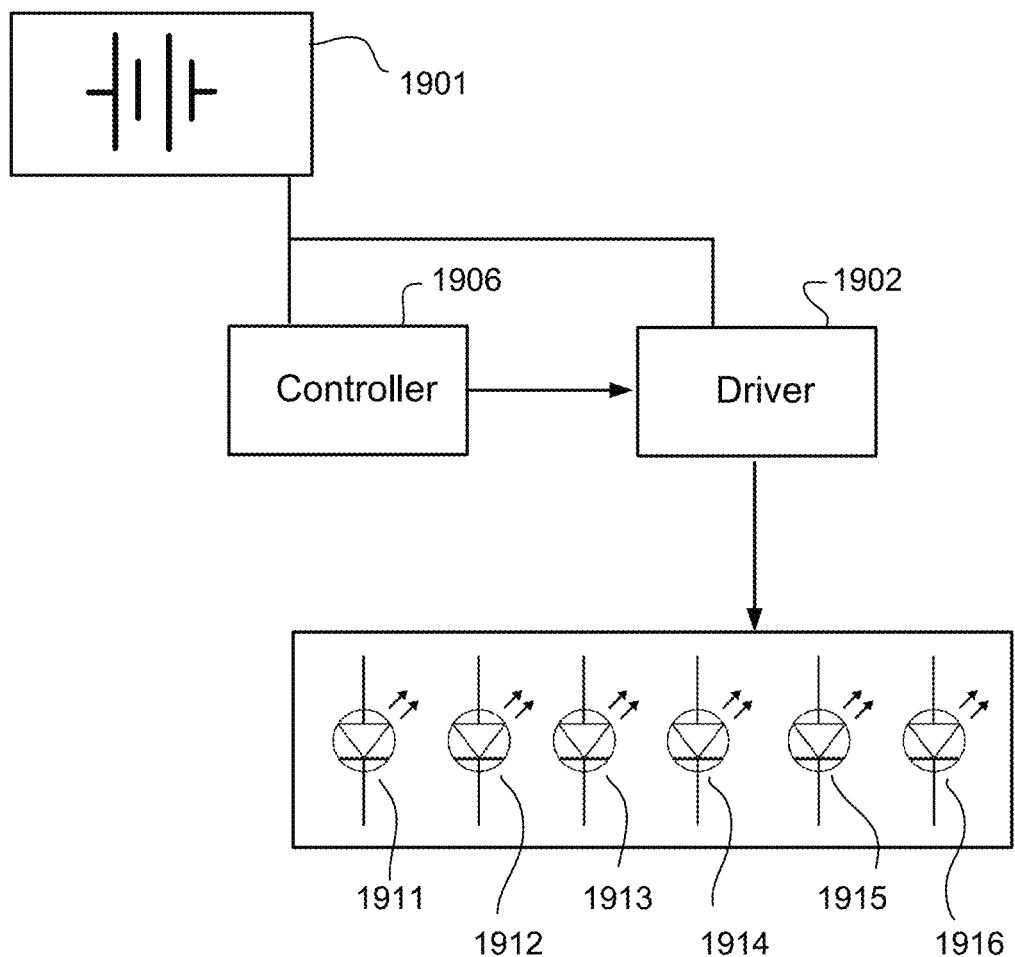
FIG. 19 is a schematic diagram of an example configuration for providing light disinfection.

FIG. 19 is a schematic diagram of an example configuration for providing light disinfection. Depicted are power source 1901, driver 1902, controller 1906 and light sources 1911-1916. Controller 1906 causes driver 1902 to power light sources 1911-1916, which provide the desired light output, using available power (power source 1901).

Figure 20:
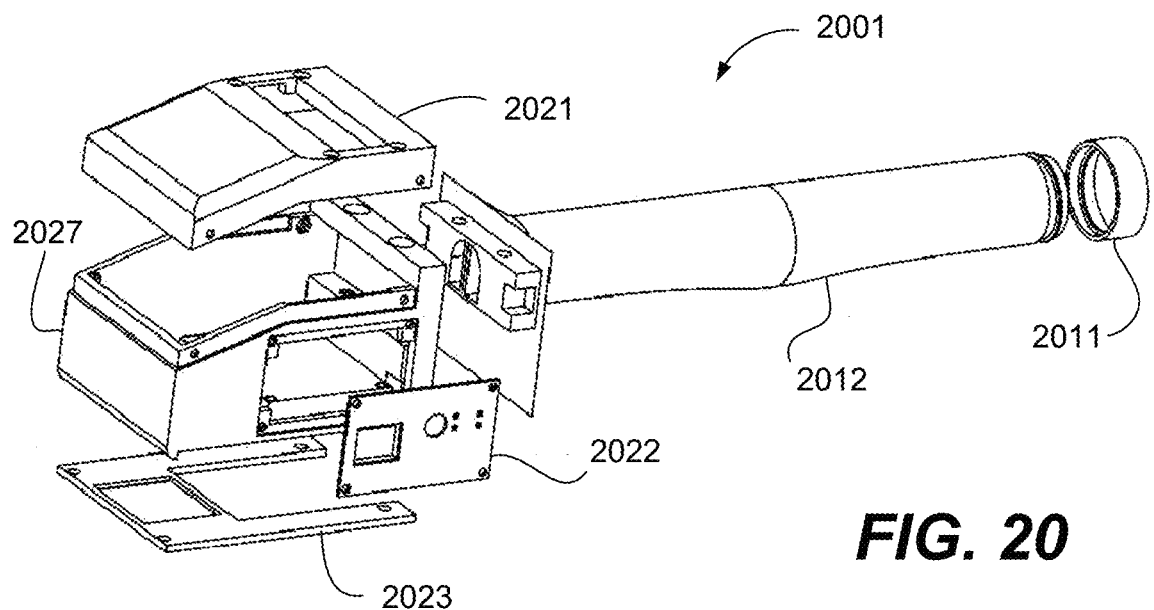
FIG. 20 is a schematic diagram showing an exploded view of a hand-held light-based disinfection device.

FIG. 20 is a schematic diagram showing an exploded view of a hand-held light-based disinfection device 2001, presented as an exploded view. Depicted are battery cover 2011, handle with battery carrier 2012, header covers 2021, 2022, 2023, and header 2027.

Figure 21:
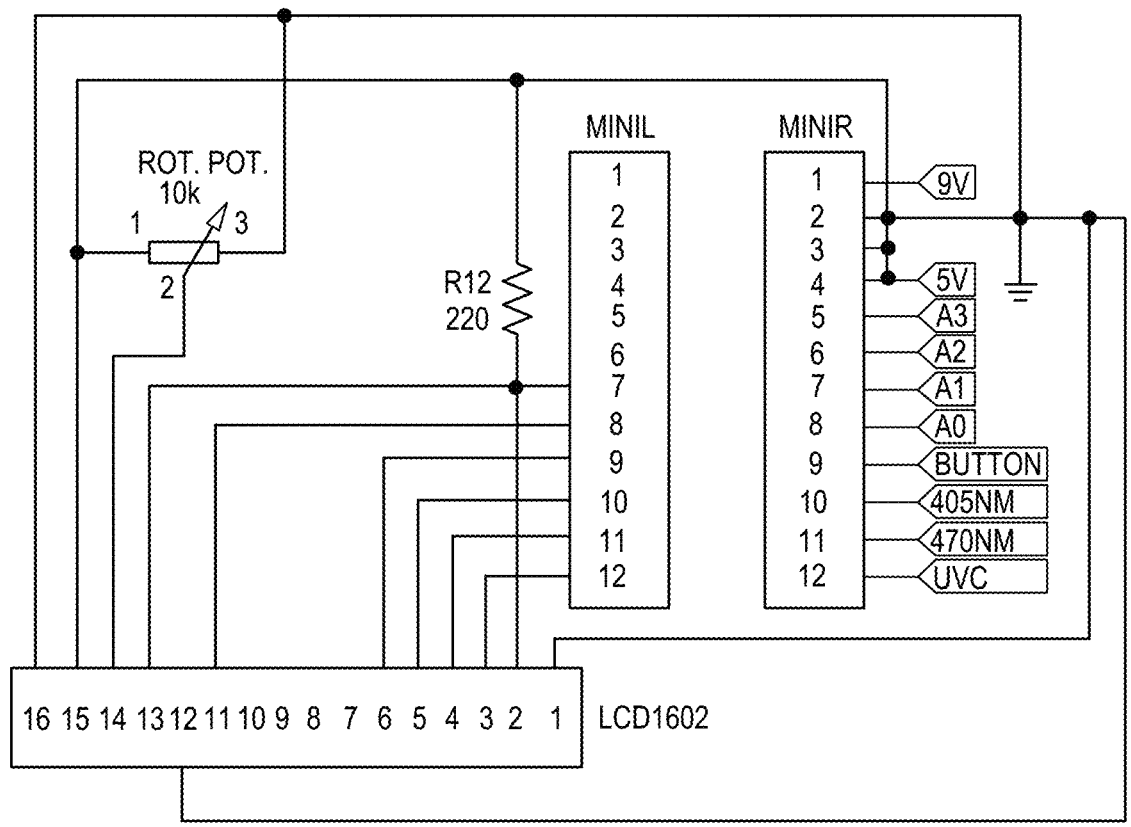
FIG. 21 is a schematic diagram showing a control circuit for light sources.

FIG. 21 is the schematic diagram of a typical control circuit for light sources. The control circuit allows adjustment of the frequency, duty cycle, illumination sequence and illumination mode (asynchronous or synchronous) of different light sources. The circuit comprises a battery connection, switch, voltage regulator, controller, power transistors to drive high intensity LEDs, and power control circuitry. The power control circuitry can comprise, by way of non-limiting example, trimmers between the digital output from the controller, voltage dividers, and hardware or software to set timing, frequency and duty cycle.

Figure 22:
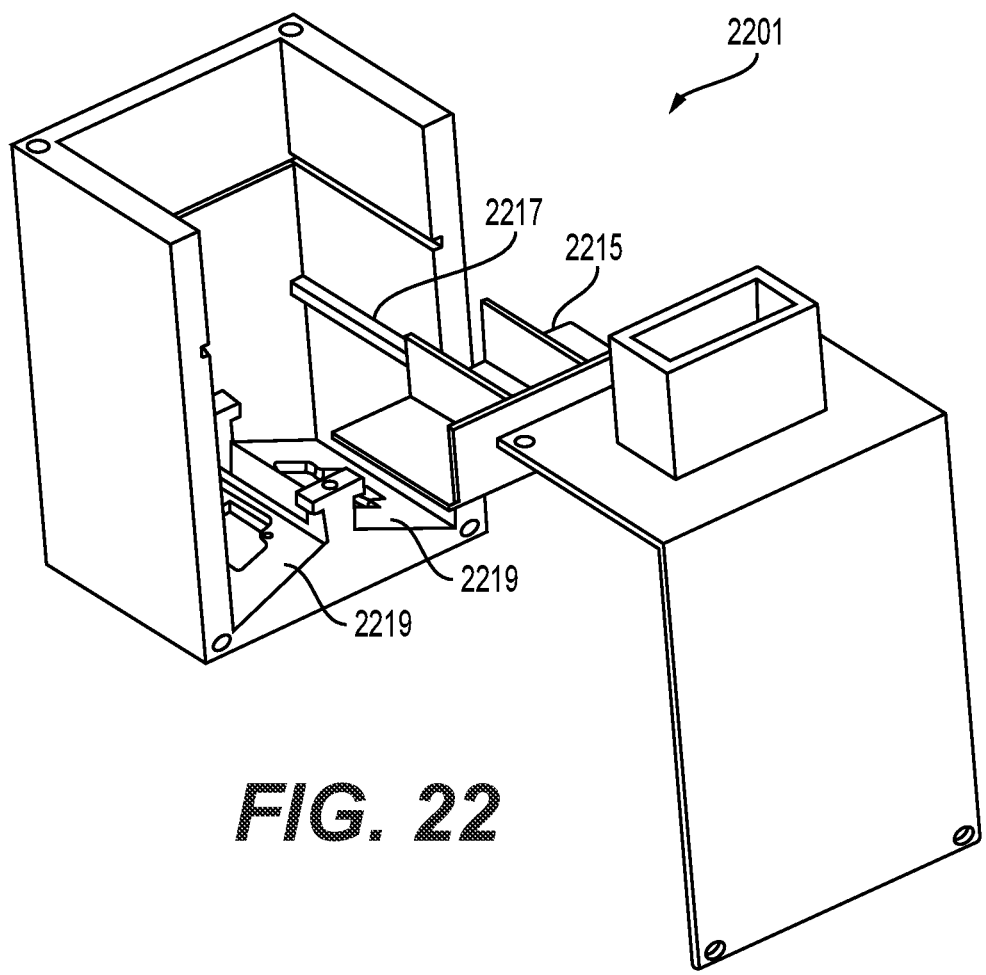
FIG. 22 is a schematic diagram showing an autonomous robot-type light-based disinfection device.

FIG. 22 shows light-based disinfection device 2201 configured to be moved by an autonomous robot (not shown). Shown are battery holder 2215 and the printed circuit board support 2217, and light source 2219. The device is attached to a machine or autonomous robots and can be self-powered so it can work independently of the machine or robot.

Figure 23:
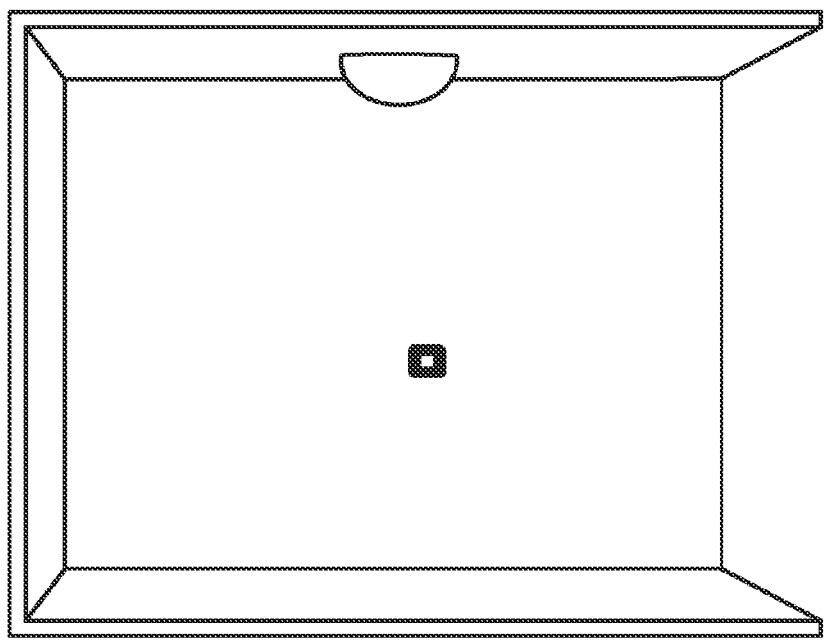
FIG. 23 is a schematic diagram of disinfection scenario using static light sources.

FIG. 23 is a schematic diagram of disinfection scenario using static light sources. This presents disinfection operation scenario using static light sources. The liquid sources are fixed on the top surface of container, drawer and biosafety cabinet.

Figure 24:
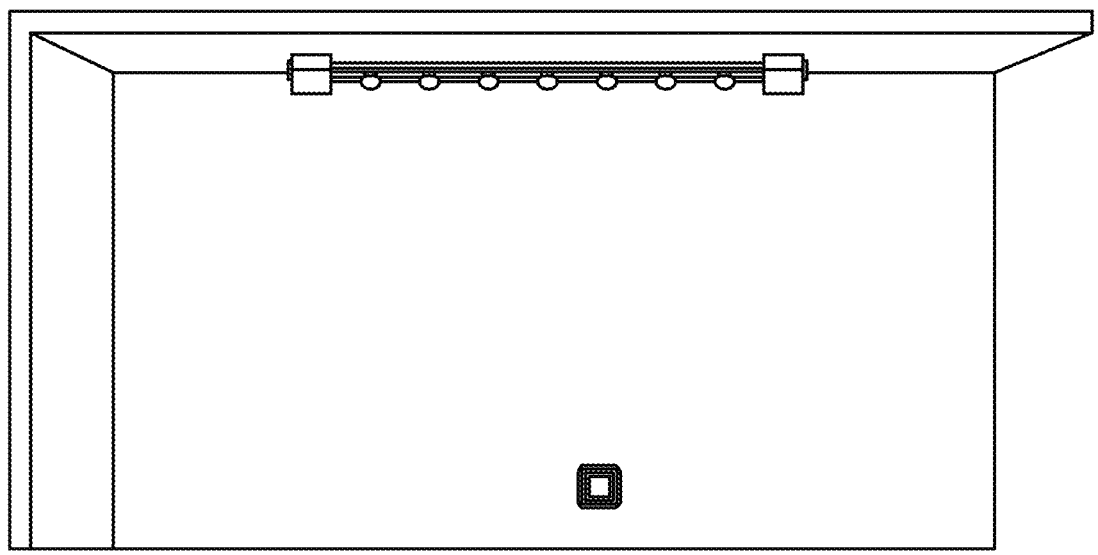
FIG. 24 is a schematic diagram of disinfection scenario using rotatory light sources.

FIG. 24 is a schematic diagram of disinfection scenario using rotatory light sources. This presents disinfection operation scenario using rotatory light sources. The light sources are fixed on the ceiling, and can rotate to focus on different areas of the room.

Figure 25:
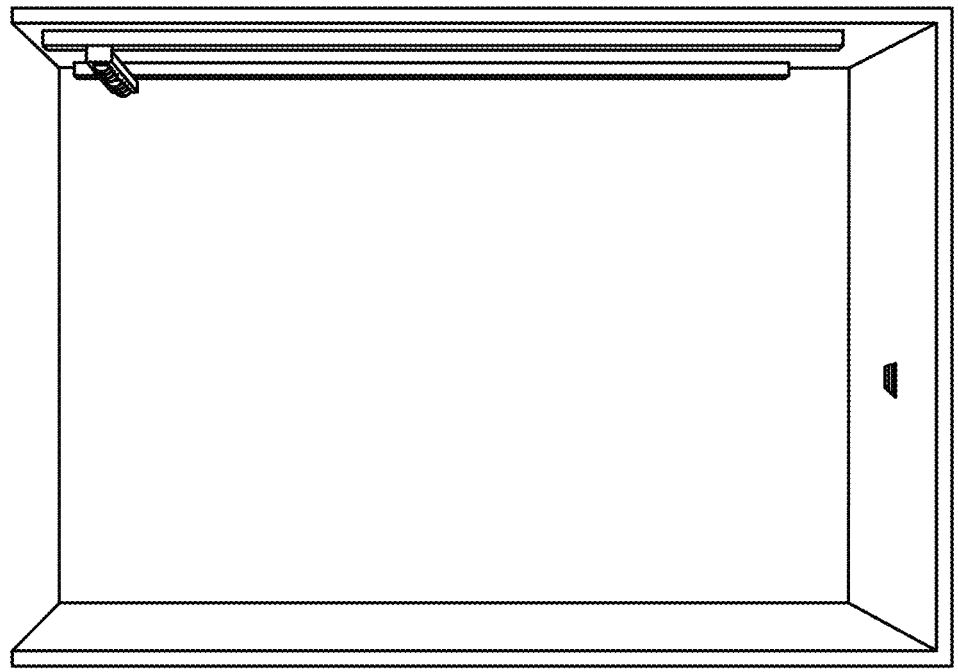
FIG. 25 is a schematic diagram of disinfection scenario using movable rail-type light sources.

FIG. 25 is a schematic diagram of disinfection scenario using movable rail-type light sources. This presents disinfection operation scenario using rail-type light sources. The light sources can move on the rail installed on the ceiling.

Figure 26:
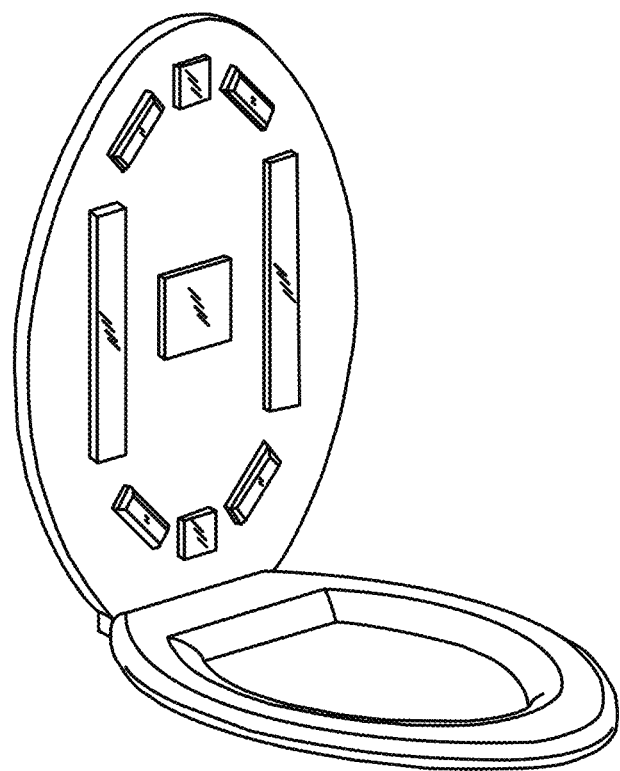
FIG. 26 is the schematic diagram of disinfection scenario in lavatory using automatic switching static light sources.

FIG. 26 is the schematic diagram of disinfection scenario in a toilet or lavatory using automatic switching static light sources. This presents disinfection operation scenario in lavatory or toilet using automatic switching static light sources. The light sources can be automatically switched on for a predetermined time when toilet cover is closed. While a toilet is depicted, it is also possible to provide a similar arrangement on other lavatory fixtures such as bidets, wash sinks, showers and other fixtures and appliances.

Figure 27:
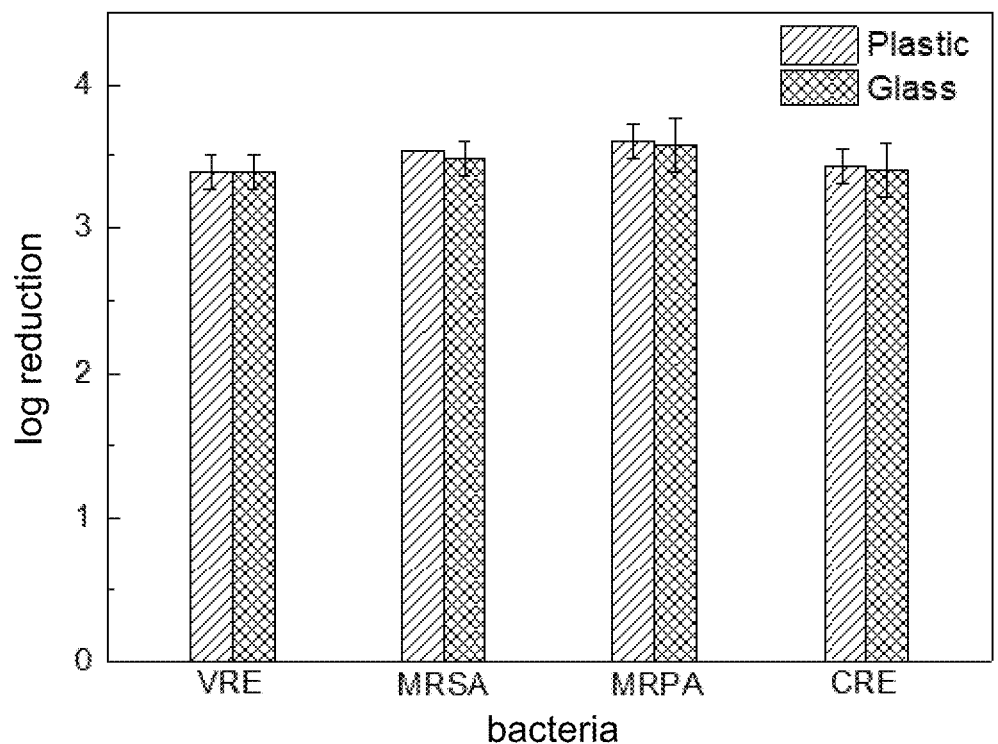
FIG. 27 is a graphical depiction presenting bactericidal activities of light-based disinfection device for different antibiotic-resistant bacteria on plastic and glass surfaces.

FIG. 27 is a graphical depiction presenting bactericidal activities of light-based disinfection device for different antibiotic-resistant bacteria on plastic and glass surfaces. The graph presents bactericidal activities of light-based disinfection device for $10^5$ CFU/ml of vancomycin-resistant *Enterococci* (VRE), methicillin-resistant *Staphylococcus aureus* (MRSA), multi-drug-resistant *Pseudomonas aeruginosa* (MRPA) and carbapenem-resistant Enterobacteriaceae (CRE) on plastic and glass surfaces. The light-based disinfection device combining blue light and UV LEDs can reduce more than 99.9% of antibiotic-resistant bacteria on plastic surface (10-min. exposure) and glass surface (15-min. exposure).

Figure 28:
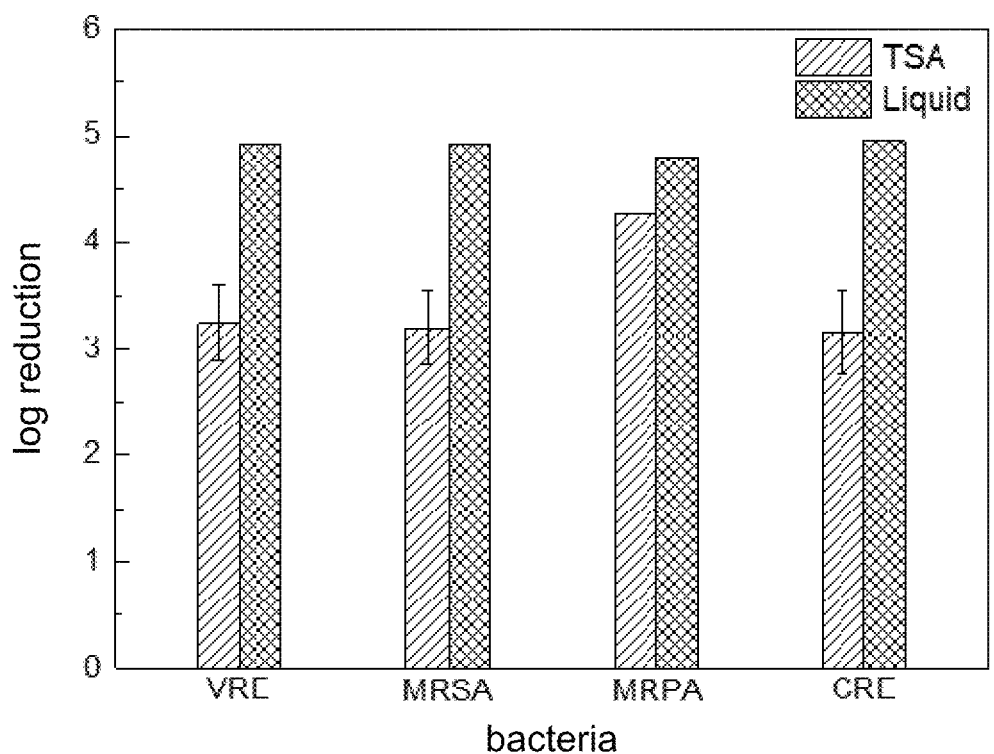
FIG. 28 is a graphical depiction presenting bactericidal activities of light-based disinfection device for antibiotic-resistant bacteria on culture media and in liquid phase.

FIG. 28 is a graphical depiction presenting bactericidal activities of light-based disinfection device for antibiotic-resistant bacteria on culture media and in liquid phase. The graph presents bactericidal activities of light-based disinfection device for $10^5$ CFU/ml of VRE, MRSA, MRPA and CRE on culture media and in liquid phase. The light-based disinfection device combining blue light and UV LEDs can reduce more than 99.8% of antibiotic-resistant bacteria on plastic surface (15-min. exposure) and more than 99.999% of antibiotic-resistant bacteria in liquid glass surface (10-min. exposure).

Figure 29A:
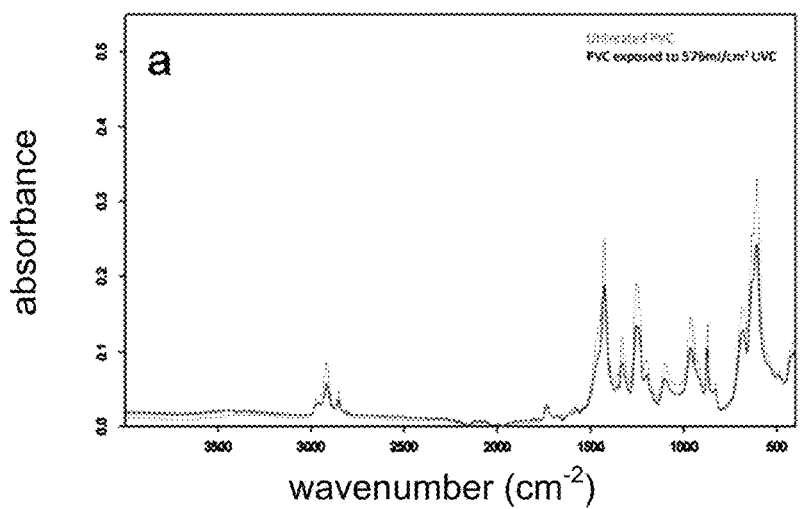
FIGS. 29A, 29B and 29C are graphic depictions comparing Fourier-transform infrared spectroscopy (FTIR) spectra of polyvinyl chloride, polystyrene and polypropylene before and after exposure to UVC.
Figure 29B:
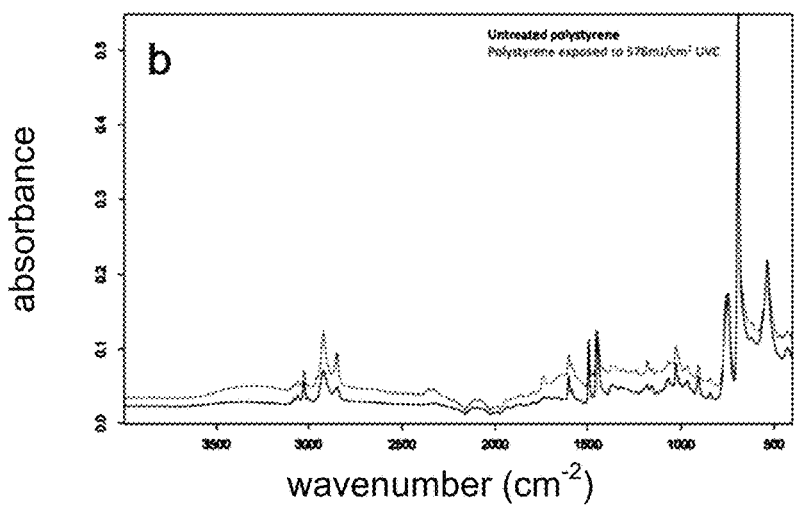
Figure 29C:
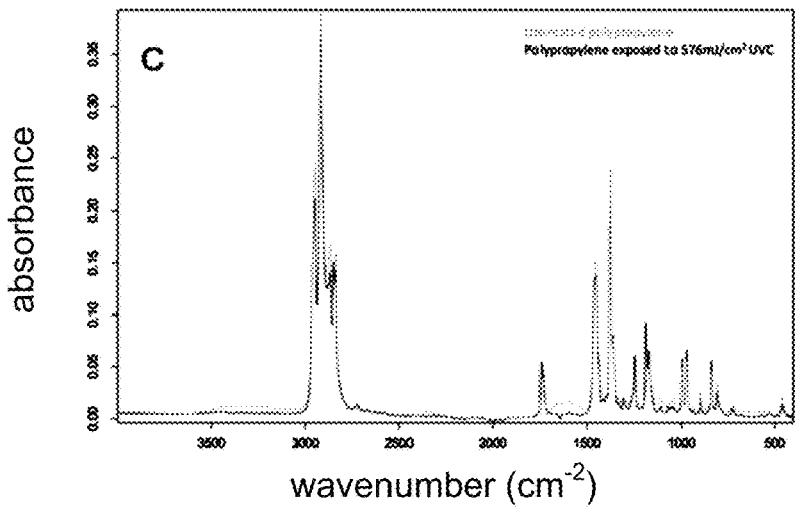

FIGS. 29A, 29B and 29C are graphic depictions comparing Fourier-transform infrared spectroscopy (FTIR) spectra of polyvinyl chloride, polystyrene and polypropylene before and after exposure to UVC (dosage: 576 mJ/cm2). No visible band shifts are observed from their FTIR spectra, which indicates that UVC light didn't damage chemical structures of these three plastics.

Figure 30A:
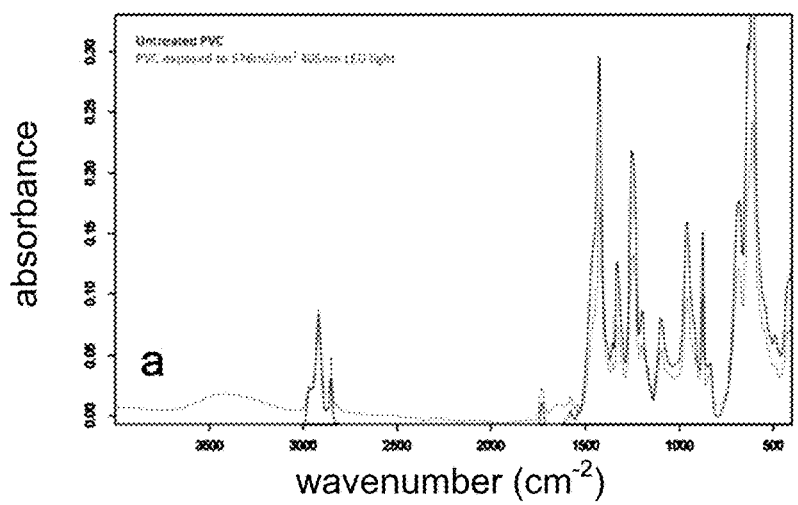
FIGS. 30A, 30B and 30C are graphic depictions comparing FTIR spectra of polyvinyl chloride, polystyrene and polypropylene before and after exposure to blue light.
Figure 30B:
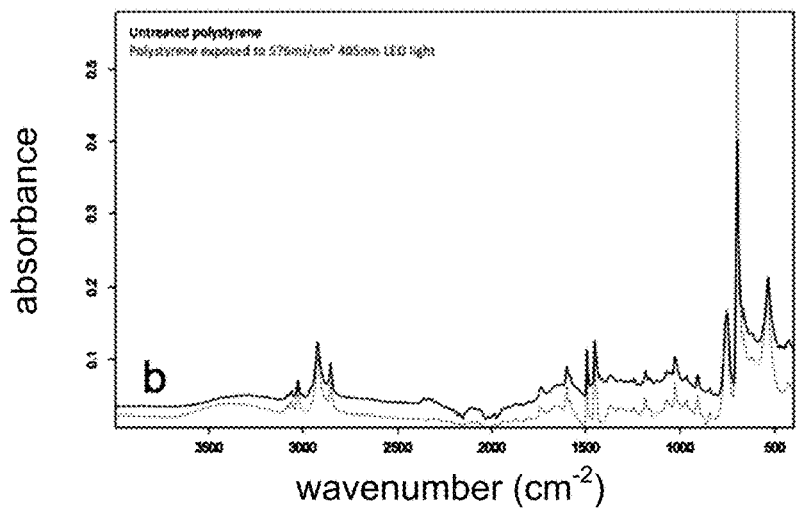
Figure 30C:
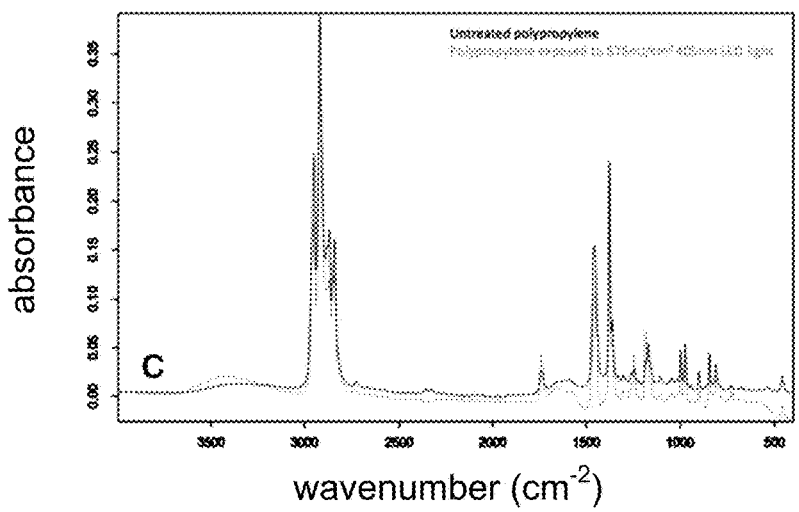

FIGS. 30A, 30B and 30C are graphic depictions comparing FTIR spectra of polyvinyl chloride, polystyrene and polypropylene before and after exposure to blue light (dosage: 576 mJ/cm2). No visible band shifts are observed from their FTIR spectra, which indicates that blue light didn't damage chemical structures of these three plastics.

Figure 31:
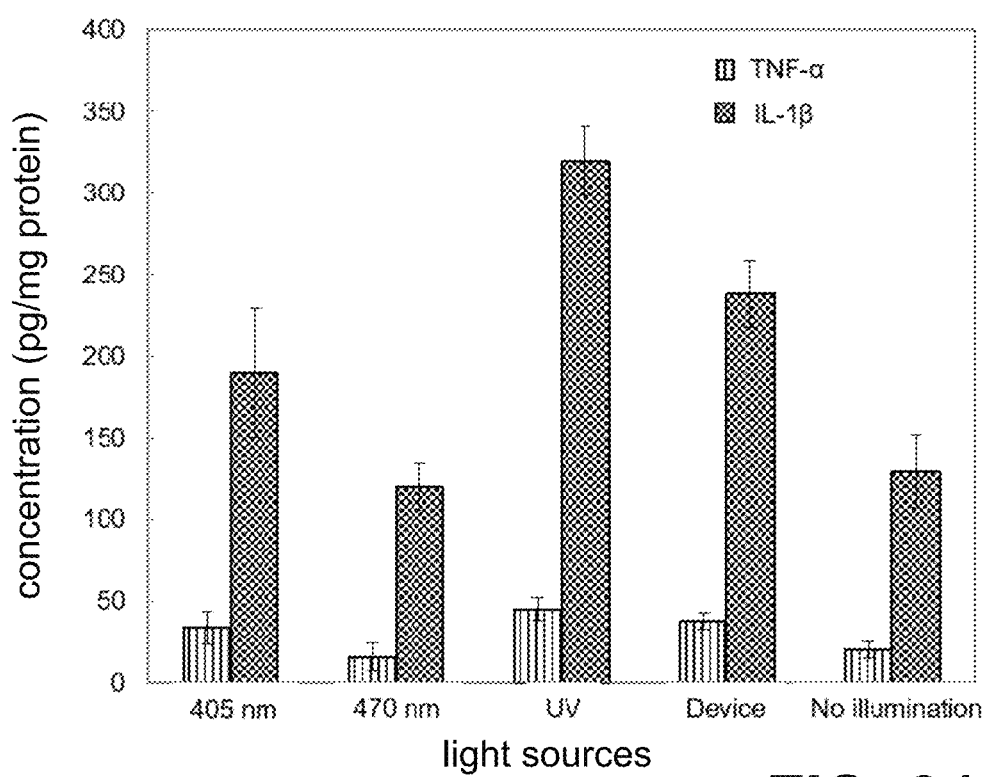
FIG. 31 is a diagram showing the levels of tumor necrosis factor-α (TNF-α) and interleukin-1β (IL-1β) in rat skins exposed to different light sources.

FIG. 31 is a diagram showing the levels of tumor necrosis factor-α (TNF-α) and interleukin-1β (IL-1β) in rat skins exposed to 405 nm blue light, 470 nm blue light, UV light and light-based disinfection device combining blue light and UV LEDs. The levels of TNF-α and IL-1β generated from exposures to 405 nm blue light, 470 nm blue light and light-based disinfection device are lower than those from exposure to UV light. The effect of exposure to 470 nm blue light is comparable with that without no illumination. The results shown in FIGS. 30A, 30B, 30C and FIG. 31 verify good material compatibility of applied light sources.

EXAMPLES

Example 1: Four Light Array

An array of four UV LEDs (UVTOP270T039FW, SETi Ltd) was built onto a breadboard for the test. Each UV LED could output UV light with a peak wavelength at 280 nm and light intensity of 5.4 μW/cm², which was measured by the spectroradiometer (ILT900-R, International Light). The array of lights was powered by the direct current power supply (GW, GPC-1850D) with 5 V and 0.7 A output. Subsequently, 5 μL of bacterial suspension ($10^7$ CFU/mL, *P. aeruginosa, E. coli, S. aureus,* or *E. faecalis*) was continuously illuminated by the UV LED array at various dosages. Samples without illumination were taken as the control. At least three samples were tested for each data point. After illumination, bacteria were recovered from each wells and cultured on a TSA plate for incubation at 37° C. for 24 h. The viable bacteria were enumerated from formed colony number. (FIGS. 2A-2D)

Example 2: Exposure of Specimens

5 μl ($10^7$ CFU/mL) of *E. coli* suspension was seeded into wells of a 96-well microplate. Subsequently, it was illuminated by a LED array with a series of wavelengths such as: 390 nm, 395 nm, 400 nm, 405 nm, 410 nm, 470 nm, 850 nm and 950 nm (UV5TZ-390-15, UV5TZ-395-15, UV5TZ-400-15, UV5TZ-405-15, UV5TZ-410-15, HLMP-CB1B-XYODD, TSHG6400 and SFH4811, RS Components Ltd). The single LEDs were mounted to a board and arranged as the 96-well plate. This LED array was powered by a direct current power supply (GW, GPC-1850D) which was set a 5 V and 20 mA output. After 60-minute illumination, bacteria were recovered from each wells. In addition, they were plated onto a Tryptone Soy Agar (TSA) plate for incubation at 37° C. for 24 h. The viable bacteria were enumerated from formed colony number. (FIG. 4)

Example 3: Pulse Lighting

The UV LEDs, described in Example 1, were controlled by a pulse generator (HP HEWLETT, 8114A) to generate pulsed lighting with 50% duty cycle and 1 Hz frequency. Subsequently, bacterial suspension ($10^7$ CFU/mL, *P. aeruginosa, E. coli, S. aureus,* or *E. faecalis*) was illuminated by the UV LED array at various dosages. Samples without illumination were taken as the control. At least three samples were tested for each data point. After illumination, bacteria were recovered from each wells, cultured and enumerated as described in Example 1. (FIGS. 6A-6E)

Example 4: Continuous Light

The UV LEDs, as described in Example 1, were controlled by the direct current power supply with 5 V and 0.7 A output to generate a continuous light. Subsequently, bacterial suspension ($10^7$ CFU/mL, *P. aeruginosa, E. coli, S. aureus,* or *E. faecalis*) was illuminated by the UV LED array at various dosages. Samples without illumination were taken as the control. At least three samples were tested for each data point. After illumination, bacteria were recovered from each wells, cultured and enumerated as described in Example 1. (FIGS. 6A-6E)

Example 5: Pulsed Blue Light

The blue light matrices with wavelength of 405 nm and 470 nm were controlled by a pulse generator (HP HEWLETT, 8114A) to generate pulsed light with 50% duty cycle and 1 Hz frequency. Meanwhile, the other group LEDs matrices were controlled by the direct current power supply to generate a continuous light. Subsequently, 5 μL of *S. aureus, E. faecalis, E. coli,* or *P. aeruginosa* ($10^7$ CFU/mL) were illuminated by the continuous and pulsed lighting, respectively. (FIG. 7)

Example 6: Pulse Light Effect on Cell Inhibition Rate

200 µl of cells (A431, Skin/Epidermis) were seeded into a 96-well plate. After growth for 24 hours, A431 were illuminated by 0.3 mJ/cm$^2$ and 3.6 mJ/cm$^2$ pulsed single UV LEDs, which were set in Example 1. An MTT assay was performed to determine cell inhibition rate. (FIGS. 8A and 8B)

Example 7: Continuous Light Effect on Cell Inhibition Rate

200 µl of A431 cells were seeded into a 96-well plate. After growth for 24 hours, A431 were illuminated by 0.3 mJ/cm$^2$ and 3.6 mJ/cm$^2$ continuous single UV LEDs, which were set in Example 1. An MTT assay was performed to determine cell inhibition rate. (FIGS. 8A and 8B)

Example 8: Pulsed and Continuous Light Effect on Cell Inhibition Rate

200 µl of A431 cells were seeded into a 96-well plate. After growth for 24 hours, A431 were illuminated by 57.6 mJ/cm$^2$ pulsed and continuous 405 nm single LEDs, which were set in Example 5. An MTT assay was performed to determine cell inhibition rate. (FIGS. 8A and 8B)

Example 9: Pulsed and Continuous Light Effect on Cell Inhibition Rate

200 µl of A431 cells were seeded into a 96-well plate. After growth for 24 hours, A431 were illuminated by 45 mJ/cm$^2$ pulsed and continuous 470 nm single LEDs, which were set in Example 5. An MTT assay was performed to determine cell inhibition rate. (FIGS. 8A and 8B)

Example 10: Pulsed and Continuous Light Effect on Cell Inhibition Rate

200 µl of A431 cells were seeded into a 96-well plate. After growth for 24 hours, A431 were illuminated by 57.6 mJ/cm$^2$ pulsed and continuous 405 nm single LEDs, which were set in Example 5. IL-8 Level of the A431 was estimated and performed by a commercial Human IL-8 ELISA assay kit (R&D Systems®, Quantikine® ELISA). (FIG. 9)

Example 11: Pulsed and Continuous Light Effect on Cell Inhibition Rate

200 µl of A431 cells were seeded into a 96-well plate. After growth for 24 hours, A431 were illuminated by 45 mJ/cm$^2$ pulsed and continuous 470 nm single LEDs, which were set in Example 5. IL-8 Level of the A431 was estimated and performed by a commercial Human IL-8 ELISA assay kit (R&D Systems®, Quantikine® ELISA). (FIG. 9)

Example 12: Pulsed and Continuous Light Effect on Cell Inhibition Rate

200 µl of A431 cells were seeded into a 96-well plate. After growth for 24 hours, A431 were illuminated by 0.3 mJ/cm$^2$ pulsed and continuous single UV LEDs lighting, which were set in Example 1. IL-8 Level of the A431 was estimated and performed by a commercial Human IL-8 ELISA assay kit (R&D Systems®, Quantikine® ELISA). (FIG. 9)

Example 13: Dark Condition

200 µl of A431 cells were seeded into a 96-well plate. After growth for 24 hours, A431 were placed in dark condition. IL-8 Level of the A431 was estimated and performed by a commercial Human IL-8 ELISA assay kit (R&D Systems®, Quantikine® ELISA). (FIG. 9)

Example 14: Pulsed Light at Different Intermittent Frequencies

The UV LEDs, described in Example 1, was controlled by a pulse generator (HP HEWLETT, 8114A) to generate pulsed light with 50% duty cycle and a series of intermittent (pulsed) frequencies (1, 10, 20, 30, 40, 50 Hz). Meanwhile, the UV LEDs were controlled by the direct current power supply to generate a continuous light. Subsequently, 5 µL of *P. aeruginosa* (10$^7$ CFU/mL) was illuminated by the continuous and pulsed lights at dosage of 0.027 mJ/cm$^2$. Control was performed without illumination. The experiment was performed at least in triplicate for each frequency. After illumination, bacteria were recovered from each wells. They were plated onto a TSA plate for incubation at 37° C. for 24 h. The viable bacteria were enumerated from formed colony number. (FIGS. 10B-10E)

Example 15: Pulsed and Continuous Light and Dark Condition

5 µL of *E. coli* (10$^7$ CFU/mL) was illuminated by the continuous and pulsed lights at various frequencies by the UV LED setup mentioned in Example 14 at dosage of 0.65 mJ/cm$^2$. Control was performed without illumination. The experiment was performed at least in triplicate for each frequency. After illumination, bacteria were recovered, cultured and enumerated as described in Example 1. (FIGS. 10B-10E)

Example 16: Pulsed and Continuous Light and Dark Condition

5 µL of *S. aureus* (10$^7$ CFU/mL) was illuminated by the continuous and pulsed lights at various frequencies by the UV LED setup mentioned in Example 14 at dosage of 1.62 mJ/cm$^2$. Control was performed without illumination. The experiment was performed at least in triplicate for each frequency. After illumination, bacteria were recovered, cultured and enumerated as described in Example 1. (FIGS. 10B-10E)

Example 17: Pulsed and Continuous Light and Dark Condition

5 µL of *E. faecalis* (10$^7$ CFU/mL) was illuminated by the continuous and pulsed lighting at various frequencies by the UV LED setup mentioned in Example 14 at dosage 2.59 mJ/cm$^2$. Control was performed without illumination. The experiment was performed as least in triplicate for each frequency. After illumination, bacteria were recovered, cultured and enumerated as described in Example 1. (FIGS. 10B-10E)

Example 18: Pulsed and Continuous Light and Dark Condition

The UV LEDs, described in Example 1, was controlled by a pulse generator (HP HEWLETT, 8114A) to generate pulsed light with 1 Hz and a series of duty cycles (20, 40, 60, 80%). Meanwhile, the UV LEDs were controlled by the direct current power supply to generate a continuous light. Subsequently, 5 µL of *P. aeruginosa* ($10^7$ CFU/mL) was illuminated by the continuous and pulsed lights at dosage of 0.027 mJ/cm². Control was performed without illumination. The experiment was performed at least in triplicate for each duty cycle. After illumination, bacteria were recovered from each wells and cultured onto a TSA plate for incubation at 37° C. for 24 h. The viable bacteria were enumerated from formed colony number. (FIGS. 11B-11E)

Example 19: Pulsed and Continuous Light and Dark Condition

5 µL of *E. coli* ($10^7$ CFU/mL) was illuminated by the continuous and pulsed lights at various duty cycles by the UV LED setup mentioned in Example 18 at dosage of 0.65 mJ/cm². Control was performed without illumination. The experiment was performed at least in triplicate for each duty cycle. After illumination, bacteria were recovered, cultured and enumerated as described in Example 2. (FIG. 11B-11E)

Example 20: Pulsed and Continuous Light and Dark Condition

5 µL of *S. aureus* ($10^7$ CFU/mL) was illuminated by the continuous and pulsed lights at various duty cycles by the UV LED setup mentioned in Example 18 at dosage of 1.62 mJ/cm². Control was performed without illumination. The experiment was performed at least in triplicate for each duty cycle. After illumination, bacteria were recovered, cultured and enumerated as described in Example 2. (FIGS. 11B-11E)

Example 21: Pulsed and Continuous Light and Dark Condition

5 µL of *E. faecalis* ($10^7$ CFU/mL) was illuminated by the continuous and pulsed lights at various duty cycles by the UV LED setup mentioned in Example 18 at dosage of 2.59 mJ/cm². Control was performed without illumination. The experiment was performed at least in triplicate for each duty cycle. After illumination, bacteria were recovered, cultured and enumerated as described in Example 2. (FIGS. 11B-11E)

Example 22: Synchronous and Asynchronous Light Patterns

A light system consisting of a 10W 405 nm LED (CL-P10WB34RSH10100, China, 9-11 V, 1000 mA), a 10W 470 nm LED (CL-P10WU64RSH1030, China, 9-11 V, 1000 mA) and 4 UV LEDs was used as the light source for production of synchronous and asynchronous light patterns. The LEDs were mounted in a heat sink with a cooling fan. The 10 W 405 nm LED emitted light with intensity of $10^5.5$ µW/cm² while the 10 W 470 nm LED emitted light with intensity of 2200 µW/cm², measured by a blue light radiometer (HANDY, FL-1D). The system was powered by three 4 V chargeable batteries and controlled by a circuit with a programmed controller (Arduino) and a monitor. Exposure time, frequency, duty cycle and light pattern were adjustable. The setup was covered to prevent background white light from reaching the samples. (FIG. 12)

Example 23: Synchronous Continuous Illumination

An agar plate of 14 cm diameter was seeded with 200 µL of *P. aeruginosa* ($10^5$ CFU/mL) was illuminated by the system mentioned in Example 22 with a synchronous light pattern with UV dosage of 0.976 mJ/cm² for 10 minutes. The synchronous light pattern was produced by applying continuous 405 nm and 470 nm lights from the 10 W LEDs and pulsed LEDs at 1 Hz and 20% duty cycle at the same time. Samples that were not exposed to the lights acted as the control. The setup was covered to prevent background white light from reaching the samples. (FIG. 13)

Example 24: Synchronous Pulsed Illumination

An agar plate of 14 cm diameter seeded with 200 µL of *P. aeruginosa* ($10^5$ CFU/mL) was illuminated by the system mentioned in Example 22, but with an asynchronous light pattern with UV dosage of 0.976 mJ/cm². The asynchronous light pattern was produced by applying alternative pulsed 405 nm and 470 nm lights from the 10 W LEDs at 1 Hz and 10% duty cycle and pulsed UV from the UV LEDs at 1 Hz and 20% duty cycle. Samples that were not exposed to the lights acted as the control. The setup was covered to prevent background white light from reaching the samples. (FIG. 13)

Example 25: Asynchronous Pulsed Illumination

It was observed that enhancement of bactericidal efficacy by asynchronous light depends on the sequence of the exposure. Lighting scheme 1 was intermitted (pulsed) UV (280 nm) LED lighting at 1 Hz pulse rate and 90% duty cycle. Exposure dosages of 0.12, 0.16, 0.24, 0.36 and 0.48 mJ/cm² on *P. aeruginosa* and 0.32, 0.48, 0.64, 0.80, 0.96 mJ/cm² on *S. aureus*. Experiments were performed at least in triplicate for each data point. Photos of the resulted plates were analyzed by an image analysis software, Image J (Image J1.5 1a, NIH), which measured the area of clearance. The clearance area from UV (280 nm) LED served as reference for comparing lighting scheme 2-7. (FIGS. 14, 15A and 15B).

Example 26: Asynchronous Pulsed Illumination

Lighting scheme 2-7 shown in FIG. 14 are examples of asynchronous lights. The lighting scheme 2 and 7 showed enhancement in bactericidal efficacy for *S. aureus* compared to UV (280) LED light according to:

$$\text{Bactericidal performance} = \frac{\% \text{ Area of inhinbtion zone caused by light combination}}{\% \text{ Area of inhibition zone caused solely by } UV \text{ light}}$$

The experiment was performed at least in triplicate for each data point. Photos of the resulted plates were analyzed by Image J (Image J1.5 1a, NIH) which measured the percentage area of inhibition zone. Effect of only UV light and blue lights acted as the benchmarks. (FIGS. 15A and 15B)

Example 27: Asynchronous Illumination

Lighting scheme 2-7 shown in FIG. 14 are examples of asynchronous lights. The lighting scheme 2 and 7 showed enhancement in bactericidal efficacy for *P. aeruginosa* compared to UV (280) LED light according to:

$$\text{Bactericidal performance} = \frac{\% \text{ Area of inhinbtion zone caused by light combination}}{\% \text{ Area of inhibition zone caused solely by } UV \text{ light}}$$

The experiment was performed at least in triplicate for each data point. Photos of the resulted plates were analyzed by Image J (Image J1.5 1a, NIH) which measured the percentage area of inhibition zone. Effect of only UV light and blue lights acted as the benchmarks. (FIGS. 15A and 15B)

Example 28: Asynchronous Illumination

An asynchronous lighting system contained one 10 W 405 nm LED (CL-P10WU64RSH1030, China), one 10 W 470 nm LED (CL-P10WB34RSH10100, China) and four UV LEDs. (FIGS. 16A, 16B, 18A, 18B and 18C)

Example 29: Asynchronous Illumination Applied to Bacteria and Viruses

Performance of the asynchronous lighting system described in Example 28 for inactivation of bacteria and viruses suggest different optimal lighting programming. (FIGS. 16A, 16B, 18A, 18B and 18C)

Example 30: Asynchronous Illumination

200 µl of A431 cells were seeded into a 96-well plate. After growth for 24 hours, A431 were exposed to the asynchronous lighting system described in Example 28 according to light programming in FIG. 16A. The IL-8 Level of the A431 was measured by a commercial Human IL-8 ELISA assay kit (R & D Systems®, Quantikine® ELISA).

Example 31: Hand-Held Device

The hand-held device integrates light sources of the specific wavelengths used in a handle device. FIG. 20 shows a non-limiting example of a hand-held configuration for a disinfecting light. The handle follows an ergonomic design and the header is designed to orient the lights to the same zone of the treatment area. The application way is as close as possible to the disinfection surface (even in direct contact) and moving it along the treatment area.

Example 32: Autonomous Robot-Type Light-Based Disinfection Device

The configuration of autonomous robot-type light-based disinfection device is shown in FIG. 22. It can be attached to an autonomous robot (e.g., cleaning robots) and disinfect the floor in the meantime the robots are performing their task.

Example 33: Disinfection Using Static Light Sources

The configuration using static light sources is used for the disinfection of container, drawer and biosafety cabinet. The light sources with different wavelengths are fixed on the top of the spaces. A controller is used, which can adjust the frequency, duty cycle, illumination sequence and illumination mode (asynchronous or synchronous) of different light sources.

Example 34: Disinfection Using Rotatory Light Sources

The configuration using rotatory light sources is used for the disinfection of small-area indoor spaces. The light sources with different wavelengths are fixed on the ceiling. A controller is used, which can adjust the frequency, duty cycle, illumination sequence, illumination mode (asynchronous or synchronous) and illumination angle of different light sources.

Example 35: Disinfection Using Movable Rail-Type Light Sources

The configuration using movable rail-type light sources is used for the disinfection of large-area indoor spaces or corridor. The light sources with different wavelengths are fixed on the rail installed on the ceiling or walls. A controller is used, which can adjust the frequency, duty cycle, illumination sequence and illumination mode (asynchronous or synchronous) of different light sources as well as movement of light sources for effective disinfection.

Example 36: Disinfection Using Automatic Switching Static Light Sources

The configuration using automatic switching static light sources is used for the disinfection of sites frequently contaminated by microorganisms such as lavatory, handrail and lift button. A controller is used, which can adjust the frequency, duty cycle, illumination sequence and illumination mode (asynchronous or synchronous) of different light sources. The controller can be triggered to automatically switch on/off light sources.

Example 37: Bactericidal Activity for VRE on Plastics

100 µl ($10^5$ CFU/ml) of vancomycin-resistant *enterococci* (VRE) suspension was seeded into 1 cm×1 cm plastic coupons. After the suspension was dried, it was illuminated by the light-based disinfection device, which combines: 10 W pulsed 405 nm (1 Hz, 10% duty cycle), 10 W pulsed 470 nm (1 Hz, 10% duty cycle) and 3 UV LEDs (1 Hz, 80% duty cycle) for 10 min. Bacteria were recovered from each coupon. Bacteria in dark condition were used as control and at least three samples were treated at each point. In addition, they were plated onto Tryptone Soy Agar (TSA) plates for incubation at 37° C. for 24 h. The viable bacteria were enumerated from formed colony number.

Example 38: Bactericidal Activity for MRSA on Plastics

100 µl ($10^5$ CFU/ml) of methicillin-resistant *Staphylococcus aureus* (MRSA) suspension was seeded into 1 cm×1 cm plastic coupons. After the suspension was dried, it was illuminated by the device mentioned in Example 37. The experimental condition and requirement were the same as those of Example 37. The viable bacteria were enumerated from formed colony number.

Example 39: Bactericidal Activity for MRPA on Plastics

100 μl ($10^5$ CFU/ml) of multiresistant *Pseudomonas aeruginosa* (MRPA) suspension was seeded into 1 cm×1 cm plastic coupons. After the suspension was dried, it was illuminated by the device mentioned in Example 37. The experimental condition and requirement were the same as those of Example 37. The viable bacteria were enumerated from formed colony number.

Example 40: Bactericidal Activity for CRE on Plastics

100 μl ($10^5$ CFU/ml) of carbapenem-resistant Enterobacteriaceae (CRE) suspension was seeded into 1 cm×1 cm plastic coupons. After the suspension was dried, it was illuminated by the device mentioned in Example 37. The experimental condition and requirement were the same as those of Example 37. The viable bacteria were enumerated from formed colony number.

Example 41: Bactericidal Activity for VRE on Glass

100 μl ($10^5$ CFU/ml) of VRE suspension was seeded into 1 cm×1 cm glass coupons. After the suspension was dried, it was illuminated by the device mentioned in Example 37 for 15 min. Bacteria were recovered from each coupon. Bacteria in dark condition was used as control and at least three samples were treated at each point. In addition, they were plated onto Tryptone Soy Agar (TSA) plates for incubation at 37° C. for 24 h. The viable bacteria were enumerated from formed colony number.

Example 42: Bactericidal Activity for MRSA on Glass

100 μl ($10^5$ CFU/mL) of MRSA suspension was seeded into 1 cm×1 cm glass coupons. After the suspension was dried, it was illuminated by the device mentioned in Example 37. The experimental condition and requirement were the same as those of Example 41. The viable bacteria were enumerated from formed colony number.

Example 43: Bactericidal Activity for MRPA on Glass

100 μl ($10^5$ CFU/ml) of MRPA suspension was seeded into 1 cm×1 cm glass coupons. After the suspension was dried, it was illuminated by the device mentioned in Example 37. The experimental condition and requirement were the same as those of Example 41. The viable bacteria were enumerated from formed colony number.

Example 44: Bactericidal Activity for CRE on Glass

100 μl ($10^5$ CFU/ml) of CRE suspension was seeded into 1 cm×1 cm glass coupons. After the suspension was dried, it was illuminated by the device mentioned in Example 37. The experimental condition and requirement were the same as those of Example 41. The viable bacteria were enumerated from formed colony number.

Example 45: Bactericidal Activity for VRE on Culture Media

100 μl ($10^5$ CFU/ml) of VRE suspension was seeded onto Tryptone Soy Agar (TSA) plates. After the suspension was dried, it was illuminated by the device mentioned in Example 37 for 15 min. Bacteria without illumination was set as control group and at least three samples were treated at each point. The treated Tryptone Soy Agar (TSA) plates were incubated at 37° C. for 24 h. The viable bacteria were enumerated from formed colony number.

Example 46: Bactericidal Activity for MRSA on Culture Media

100 μl ($10^5$ CFU/ml) of MRSA suspension was seeded onto Tryptone Soy Agar (TSA) plates. After the suspension was dried, it was illuminated by the device mentioned in Example 37. The experimental condition and requirement were the same as those of Example 45. The viable bacteria were enumerated from formed colony number.

Example 47: Bactericidal Activity for MRPA on Culture Media

100 μl ($10^5$ CFU/ml) of MRPA suspension was seeded onto Tryptone Soy Agar (TSA) plates. After the suspension was dried, it was illuminated by the device mentioned in Example 37. The experimental condition and requirement were the same as those of Example 45. The viable bacteria were enumerated from formed colony number.

Example 48: Bactericidal Activity for CRE on Culture Media

100 μl ($10^5$ CFU/ml) of CRE suspension was seeded onto Tryptone Soy Agar (TSA) plates. After the suspension was dried, it was illuminated by the device mentioned in Example 37. The experimental condition and requirement were the same as those of Example 45. The viable bacteria were enumerated from formed colony number.

Example 49: Bactericidal Activity for VRE in Liquid Phase 5 ml ($10^5$ CFU/mL) of VRE suspension was added into Petri dishes. It was illuminated by the device mentioned in Example 37 for 15 min. Bacteria in dark condition was used as control and at least three samples were treated at each point. In addition, they were plated onto Tryptone Soy Agar (TSA) plates for incubation at 37° C. for 24 h. The viable bacteria were enumerated from formed colony number.

Example 50: Bactericidal Activity for MRSA in Liquid Phase 5 ml ($10^5$ CFU/ml) of MRSA suspension was added into Petri dishes. It was illuminated by the device mentioned in Example 37. The experimental condition and requirement were the same as those of Example 47. The viable bacteria were enumerated from formed colony number.

Example 51: Bactericidal Activity for MRPA in Liquid Phase 5 ml ($10^5$ CFU/ml) of MRPA suspension was added into Petri dishes. It was illuminated by the device mentioned in Example 37. The experimental condition and requirement were the same as those of Example 47. The viable bacteria were enumerated from formed colony number.

Example 52: Bactericidal Activity for CRE in Liquid Phase 5 ml ($10^5$ CFU/ml) of CRE suspension was added into Petri dishes. It was illuminated by the device mentioned in Example 37. The experimental condition and requirement were the same as those of Example 47. The viable bacteria were enumerated from formed colony number.

Example 53: Sporicidal Activity for *Aspergillus niger* in Liquid Phase 2 ml ($10^3$ CFU/ml) of *Aspergillus niger* suspension was added into Petri dishes. It was illuminated by the device mentioned in Example 37. The experimental condition and requirement were the same as those of Example 47 for 10 min, 30 min and 60 min. The viable spores were enumerated from formed colony number.

Example 54: Virucidal Activity for *E. coli* Bacteriophage T3 on Glass

*E. coli* bacteriophage T3 suspension ($10^6$ PFU/ml) was spread on glass slides (2.5 cm×2.5 cm) to reach $10^5$ PFU loading. It was illuminated by the device mentioned in Example 37. The experimental condition and requirement were the same as those of Example 47 for 1 min, 2 min, 5 min, and 10 min. After illumination, the glass slide was thoroughly washed by 10 ml neutralizer in a 100 ml glass bottle. The obtained suspension (100 µl) was mixed with host bacterial suspension, followed by addition of semi-solid TSA and pouring the mixture onto TSA plates. The solidified plates were incubated at 37° C. for 18 h to count plaque number.

Example 55: Material Compatibility

Plastic coupons with the size of 2.5 cm×2.5 cm were tested by exposing them to UV and blue light LED to test material compatibility. For UV light test, plastic coupons were placed under light source with the intensity of 900 µW/cm². For blue light test, plastic coupons were placed under 405 nm LED array with the intensity of 32 µW/cm². The total test dosage was 576 mJ/cm². Fourier transform infrared spectra of untreated and exposed plastic coupons were recorded to evaluate the change of their chemical structures.

Example 56: Biosafety

Five groups of rats were selected to assess biosafety of light exposure to different light sources: 405 nm blue light, 470 nm blue light, UVC, the device mentioned in Example 37, and no illumination. The back hairs of rats were removed, and nude skins were exposed to different light sources with dosage of 0.1 J/cm²/day for 30 days. The levels of tumor necrosis factor-α (TNF-α) and interleukin-1β(IL-1β) in rat skins were measured using ELISA kit to determine the inflammatory response after light exposure.

CLOSING STATEMENT

From the above, it can be seen that a variety of wavelengths cycle times and energy of illumination can be used. By way of non-limiting example, the light can be provided at different wavelengths between 360 nm and 950 nm, and at ultraviolet wavelengths below 360 nm. A narrower range would provide light at different wavelengths between 360 nm and 530 nm, and at ultraviolet wavelengths between 100 nm and 360 nm. A narrower set of wavelengths would be between 360 nm and 470 nm, with ultraviolet wavelengths above 240 nm and below 360 nm. The light energy at each wavelength can range from 0.005 mJ/cm² to 1000 mJ/cm², with other possible ranges being 0.02 mJ/cm² to 60 mJ/cm², and 0.02 mJ/cm² to 60 mJ/cm². The pulse duration is limited by the time available for disinfection and the available power, with typical duty cycles ranging from 5% to 80%.

In a further example, light from LED light sources having single wavelengths ranging from 200 nm to 410 nm, from 275 nm to 285 nm, and from 465 nm to 475 nm and having spectral widths narrower than 100 nm are used. While simultaneous operation of the light sources is described, it is possible to drive the light sources so that the duty cycles of the different light sources causes the light sources to operate asynchronously to one another.

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. Apparatus for providing microbial disinfection, the apparatus comprising:
    a power source providing asynchronous, intermittent power;
    a plurality of narrow wavelength light sources, having a narrow wavelength characteristics consistent with the spectral widths of a group of single color LEDs, driven by the power source and operating at duty cycles corresponding to the asynchronous, intermittent power, said narrow wavelength light sources comprising:
        a single wavelength LED light source having a wavelength range from 465 nm to 475 nm and a spectral width narrower than 100 nm,
        and at least one narrow wavelength light source selected from a group consisting of
        a single wavelength LED light source having a wavelength range from 200 nm to 410 nm and a spectral width narrower than 100 nm, and
        a single wavelength LED light source having a wavelength range from 275 nm to 285 nm and a spectral width narrower than 100 nm;
    a controller operatively connected to the power source and configured to provide the asynchronous, intermittent power, and driving the plurality of light sources to provide asynchronous, intermittent lighting at plural narrow wavelengths to provide a sufficiently high intensity for rapid microbial disinfection process, while reducing the average energy consumption required for microbial disinfection during the microbial disinfection process by targeting multiple cellular sites along different inactivation pathways; and
    the controller configured to adjust a frequency, duty cycle, and illumination sequence of the plurality of narrow wavelength light sources.

2. The apparatus of claim 1, wherein the controller provides the asynchronous, intermittent power to provide the asynchronous, intermittent lighting at an illumination rate of 0.1 Hz to 1000 Hz and a duty cycle of 1% to 99%.

3. The apparatus of claim 1, wherein a first of said narrow wavelength light sources provides intermittent power to provide the intermittent lighting to the LED light source having a wavelength range from 200 nm to 410 nm at a duty cycle of 10% to 30%.

4. The apparatus of claim 1, wherein a first of said narrow wavelength light sources provides intermittent power to provide the intermittent lighting to the LED light source having a wavelength range from 275 nm to 285 nm at a duty cycle of 10% to 30%.

5. The apparatus of claim 1, wherein a first of said narrow wavelength light sources provides intermittent power to provide the intermittent lighting to the LED light source having a wavelength range from 465 nm to 475 nm at a duty cycle of 10% to 80%.

6. The apparatus of claim 1, further comprising:
the controller providing the asynchronous, intermittent power to provide the asynchronous, intermittent lighting at an illumination rate of 0.1 Hz to 100 Hz and a duty cycle of 10% to 99%; and
the lighting comprising UV at approximately 280 nm and light at approximately 405 nm and approximately 470 nm, with at least two of light sources implemented as LED lighting.

7. The apparatus of claim 1, further comprising:
the controller providing the asynchronous, intermittent power to apply the asynchronous, intermittent lighting at an illumination rate of 0.1 Hz to 100 Hz and a duty cycle of 10% to 99%.

8. Apparatus for providing microbial disinfection, the apparatus comprising:
a power source providing asynchronous, intermittent power;
at least three narrow wavelength light sources, having a narrow wavelength characteristics consistent with the spectral widths of a group of single color LEDs, driven by the power source and operating at duty cycles corresponding to the asynchronous, intermittent power, said three narrow wavelength light sources comprising:
a single wavelength LED light source having a wavelength range from 200 nm to 410 nm and a spectral width narrower than 100 nm,
a single wavelength LED light source having a wavelength range from 275 nm to 285 nm and a spectral width narrower than 100 nm, and
a single wavelength LED light source having a wavelength range from 465 nm to 475 nm and a spectral width narrower than 100 nm;
a controller operatively connected to the power source and configured to provide the asynchronous, intermittent power, and driving the three light sources to provide asynchronous, intermittent lighting at three narrow wavelengths to provide a sufficiently high intensity for rapid microbial disinfection process, while reducing the average energy consumption required for microbial disinfection during the microbial disinfection process by targeting multiple cellular sites along different inactivation pathways; and
the controller configured to adjust a frequency, duty cycle, and illumination sequence of the three narrow wavelength light sources.

9. The apparatus of claim 8, wherein the controller provides the asynchronous, intermittent power to provide the asynchronous, intermittent lighting at an illumination rate of 0.1 Hz to 1000 Hz and a duty cycle of 1% to 99%.

10. The apparatus of claim 8, wherein a first of said narrow wavelength light sources provides intermittent power to provide the intermittent lighting to the LED light source having a wavelength range from 200 nm to 410 nm at a duty cycle of 10% to 30%.

11. The apparatus of claim 8, wherein a first of said narrow wavelength light sources provides intermittent power to provide the intermittent lighting to the LED light source having a wavelength range from 275 nm to 285 nm at a duty cycle of 10% to 30%.

12. The apparatus of claim 8, wherein a first of said narrow wavelength light sources provides intermittent power to provide the intermittent lighting to the LED light source having a wavelength range from 465 nm to 475 nm at a duty cycle of 10% to 80%.

13. The apparatus of claim 8, further comprising:
the controller providing the asynchronous, intermittent power to provide the asynchronous, intermittent lighting at an illumination rate of 0.1 Hz to 100 Hz and a duty cycle of 10% to 99%; and
the lighting comprising UV at approximately 280 nm and light at approximately 405 nm and approximately 470 nm, with at least two of light sources implemented as LED lighting.

14. The apparatus of claim 8, further comprising:
the controller providing the asynchronous, intermittent power to apply the asynchronous, intermittent lighting at an illumination rate of 0.1 Hz to 100 Hz and a duty cycle of 10% to 99%.

15. A method for microbial disinfection comprising:
utilizing the apparatus of claim 11 to provide continuous lighting, asynchronous intermittent lighting or synchronous intermittent lighting using said plurality of wavelength light sources, with at least one of the light sources having a narrow wavelength characteristic consistent with the spectral widths of single color LEDs, wherein the lighting provides a sufficiently high intensity for rapid microbial disinfection process, while reducing the average energy consumption for microbial disinfection during the microbial disinfection process by targeting multiple cellular sites along different inactivation pathways.

16. The method of claim 15, further comprising using, as at least one of the narrow wavelength light sources, a single wavelength LED light source having a wavelength range from 200 nm to 2000 nm and a spectral width narrower than 100 nm.

17. The method of claim 15, further comprising applying the asynchronous, intermittent lighting in an exposure dosage range of 0.005 mJ/cm$^2$ to 1000 mJ/cm$^2$.

18. The method of claim 15, further comprising applying the asynchronous, intermittent lighting at an illumination rate of 0.1 Hz to 1000 Hz and a duty cycle of 1% to 99%.

19. The method of claim 15, further comprising applying the asynchronous, intermittent lighting at an illumination rate of 0.1 Hz to 100 Hz and a duty cycle of 10% to 99%.

20. The method of claim 15, wherein the process inactivates antibiotic-resistant bacteria and the antibiotic-resistant bacteria comprise vancomycin-resistant *Enterococci*, methicillin-resistant *Staphylococcus aureus*, multi-drug-resistant *Pseudomonas aeruginosa* and carbapenem-resistant *Enterobacteriaceae*.

* * * * *